(12) United States Patent
Irwin et al.

(10) Patent No.: US 7,176,218 B2
(45) Date of Patent: Feb. 13, 2007

(54) STEREOISOMERIC COMPOUNDS AND METHODS FOR THE TREATMENT OF GASTROINTESTINAL AND CENTRAL NERVOUS SYSTEM DISORDERS

(75) Inventors: Ian Irwin, Palo Alto, CA (US); Monica Palme, San Jose, CA (US); Cyrus Becker, San Francisco, CA (US)

(73) Assignee: ARYx Therapeutics, Fremont, CA (US)

( * ) Notice: Subject to any disclaimer, the term of this patent is extended or adjusted under 35 U.S.C. 154(b) by 226 days.

(21) Appl. No.: 11/031,623

(22) Filed: Jan. 7, 2005

(65) Prior Publication Data

US 2005/0176757 A1    Aug. 11, 2005

Related U.S. Application Data

(60) Provisional application No. 60/560,938, filed on Apr. 9, 2004, provisional application No. 60/534,892, filed on Jan. 7, 2004.

(51) Int. Cl.
*A01N 43/90* (2006.01)
*A61K 31/44* (2006.01)
*C07D 453/02* (2006.01)

(52) U.S. Cl. .................... 514/305; 546/137
(58) Field of Classification Search ............... 546/137; 514/305
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,870,074 A | 9/1989 | Kon et al. | |
| 4,962,115 A | 10/1990 | Van Daele | |
| 4,975,439 A | 12/1990 | Van Daele et al. | |
| 5,041,454 A | 8/1991 | Van Daele et al. | |
| 5,057,525 A | 10/1991 | Van Daele | |
| 5,137,896 A | 8/1992 | Van Daele | |
| 5,395,832 A | 3/1995 | Ito et al. | |
| 5,423,872 A | 6/1995 | Cigaina | |
| 5,500,422 A | 3/1996 | Ito et al. | |
| 5,618,828 A | 4/1997 | Gray et al. | |
| 5,629,328 A | 5/1997 | Gray et al. | |
| 5,629,329 A | 5/1997 | Gray et al. | |
| 5,705,498 A | 1/1998 | Gaster et al. | |
| 5,712,293 A | 1/1998 | McCullough et al. | |
| 5,739,151 A | 4/1998 | McCullough et al. | |
| 5,877,188 A | 3/1999 | McCullough et al. | |
| 5,877,189 A | 3/1999 | McCullough et al. | |
| 5,955,477 A | 9/1999 | Gray et al. | |
| 5,955,478 A | 9/1999 | Gray et al. | |
| 6,066,654 A | 5/2000 | Gray et al. | |
| 6,114,356 A | 9/2000 | McCullough et al. | |
| 6,147,093 A | 11/2000 | McCullough et al. | |
| 6,242,465 B1 | 6/2001 | McCullough et al. | |
| 6,331,401 B1 | 12/2001 | Gerald et al. | |
| 6,552,046 B2 | 4/2003 | Druzgala et al. | |
| 6,632,827 B2 | 10/2003 | McCullough et al. | |
| 6,638,951 B1 | 10/2003 | Kato et al. | |
| 2003/0216387 A1 | 11/2003 | Druzgala et al. | |
| 2004/0092511 A1 | 5/2004 | Billstein et al. | |

FOREIGN PATENT DOCUMENTS

| | | |
|---|---|---|
| DE | 19933926 | 1/2001 |
| EP | 0076530 A2 | 4/1983 |
| EP | 0309043 A2 | 3/1989 |
| EP | 0640601 A1 | 3/1994 |
| EP | 1149832 | 10/2001 |
| GB | 1425706 | 2/1976 |
| JP | 11292846 | 10/1999 |
| WO | WO-99/02496 | 1/1999 |

(Continued)

OTHER PUBLICATIONS

Paakkari et al., Toxicology Letters, "Cardiotoxicity of new antihistamines and cisapride", 2002, vol. 127, pp. 279-284.*

(Continued)

*Primary Examiner*—Thomas McKenzie
*Assistant Examiner*—Niloofar Rahmani
(74) *Attorney, Agent, or Firm*—McDonnell Boehnen Hulbert & Berghoff LLP

(57) ABSTRACT

The subject invention provides stereoisomeric compounds of formula (X):

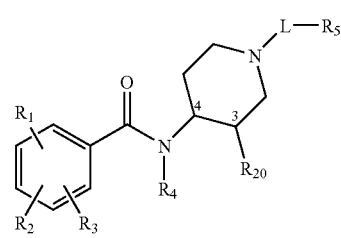

wherein the variables are as defined herein, and compositions for the safe and effective treatment of various gastrointestinal disorders including, but not limited to, gastroparesis, gastroesophageal reflux and related conditions. The compounds of the subject invention are also useful in treating a variety of conditions involving the central nervous system.

32 Claims, 2 Drawing Sheets

FOREIGN PATENT DOCUMENTS

WO    WO-01/093849-A3 F    12/2001

OTHER PUBLICATIONS

Barnes, N.M., et al. (Apr. 5, 1998) "Identification of 5-HT .sub.3 recognition sites in the ferret area postrema", J. Pharm. Pharmacol. 40:586-588.

Decktor, Dennis, et al. (1988) "Effect of metoclopramide, bethanechol and the cholecystokinin receptor antagonist, L-364,718, on gastric emptying in the rat", European Journal of Pharmacology 147:313-316.

Stacher, Georg, et al. (Nov. 1987) "Effects of Oral Cisapride on Interdigestive jejunal Motor Activity, Psychomotor Function, and Side-Effect Profile in Healthy Man", Digestive Diseases and Sciences 32(11):1223-1230.

Van Daele, Georges H.P., et al. (1986) "Synthesis of Cisapride, a Gastrointestinal Stimulant Derived From Cis-4-Amino-3-Methoxypiperidine", Drug Development Research 8:225-232.

Sanger et al., "Preparation of substituted indol-3-yl . . . " CA 119:72611 (1993).

Dean et al., "No change in the density of serotonin 1a . . . " CA 131:30595 (1999).

Sakurai et al., "Involvement of the 5-hydroxytryptamine 4 . . . " CA 139:115744 (2003).

Stoinov et al., "Evaluation of the effects of the medications . . . " CA 135:251747 (2001).

Ohuchi et al., "Preparation of quinolinecarboxylic . . . " CA 124:202043 (1996).

\* cited by examiner

Figure 1: Concentration-Response Curves for 5-HT$_4$ Receptor Agonism
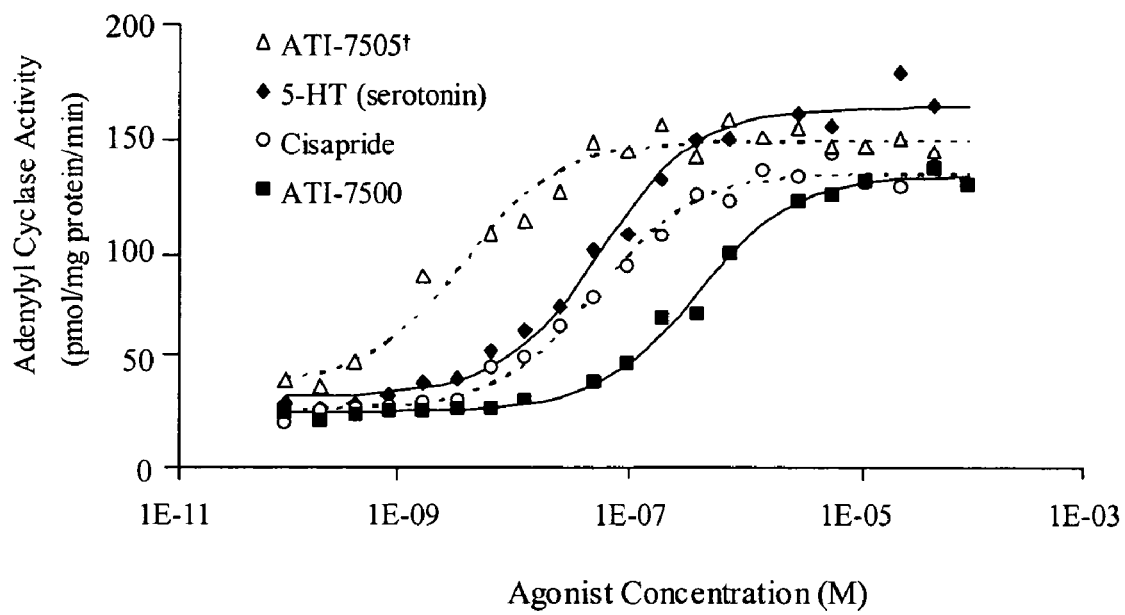
Figure 2: Gastric Emptying in Fed Dogs
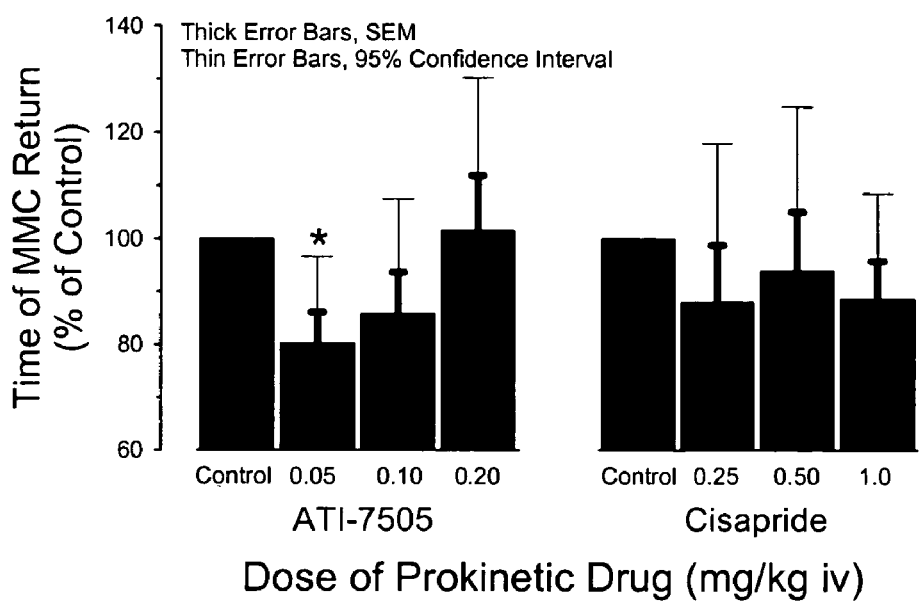

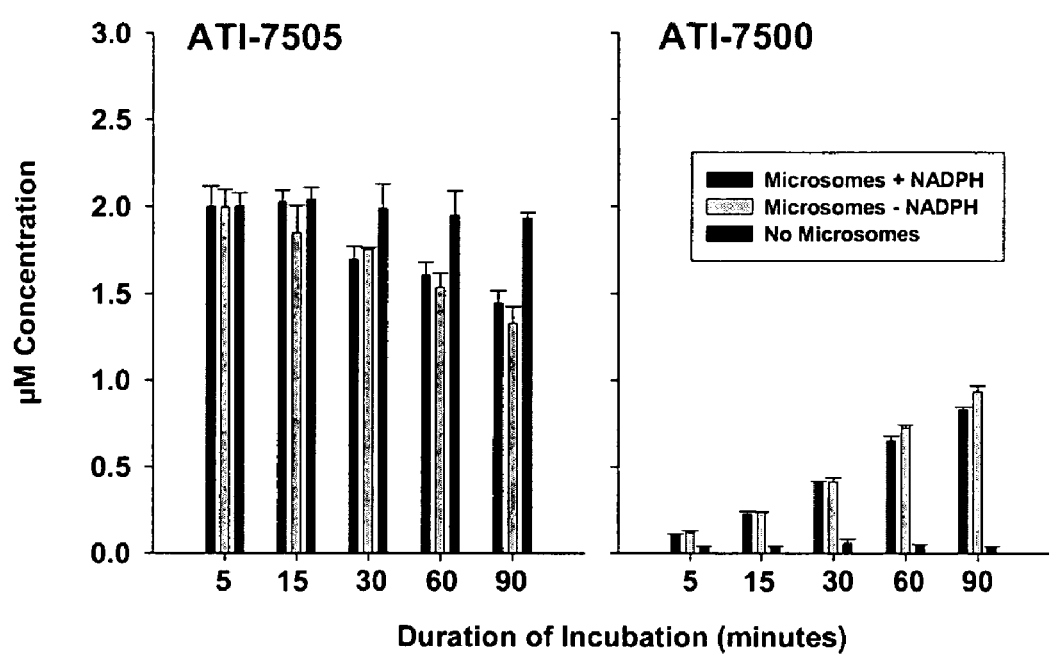
Figure 3. Metabolism With and Without the CYP450-Dependent Cofactor, NADPH

STEREOISOMERIC COMPOUNDS AND METHODS FOR THE TREATMENT OF GASTROINTESTINAL AND CENTRAL NERVOUS SYSTEM DISORDERS

This application claims priority from U.S. Provisional Patent Application No. 60/534,892, filed Jan. 7, 2004, and U.S. Provisional Patent Application No. 60/560,938, filed Apr. 9, 2004.

BACKGROUND OF INVENTION

Cisapride is one of a class of compounds known as benzamide derivatives, the parent compound of which is metoclopramide. U.S. Pat. Nos. 4,962,115 and 5,057,525 (collectively "Van Daele" and incorporated by reference in their entireties) disclose N-(3-hydroxy-4-piperidenyl)benzamides of cisapride. Van Daele discloses that these compounds, the pharmaceutically acceptable acid addition salts thereof and the stereochemically isomeric forms thereof, stimulate the motility of the gastrointestinal system.

As a class, these benzamide derivatives have several prominent pharmacological actions. The prominent pharmacological activities of the benzamide derivatives are due to their effects on the neuronal systems which are modulated by the neurotransmitter serotonin. The role of serotonin, and thus the pharmacology of the benzamide derivatives, has been broadly implicated in a variety of conditions for many years. Thus, research has focused on locating the production and storage sites of serotonin as well as the location of serotonin receptors in the human body in order to determine the connection between these sites and various disease states or conditions.

In this regard, it was discovered that a major site of production and storage of serotonin is the enterochromaffin cell of the gastrointestinal mucosa. It was also discovered that serotonin has a powerful stimulating action on intestinal motility by stimulating intestinal smooth muscle, speeding intestinal transit, and decreasing absorption time, as in diarrhea. This stimulating action is also associated with nausea and vomiting.

Because of their modulation of the serotonin neuronal system in the gastrointestinal tract, many of the benzamide derivatives are effective anti-emetic agents and are commonly used to control vomiting during cancer chemotherapy or radiotherapy, especially when highly emetogenic compounds such as cisplatin are used. This action is almost certainly the result of the ability of the compounds to block the actions of serotonin (5HT) at specific sites of action, called the $5HT_3$-receptor, which was classically designated in the scientific literature as the serotonin M-receptor. Chemotherapy and radiation therapy may induce nausea and vomiting by the release of serotonin from damaged enterochromaffin cells in the gastrointestinal tract. Release of the neurotransmitter serotonin stimulates both afferent vagal nerve fibers (thus initiating the vomiting reflex) and serotonin receptors in the chemoreceptor trigger zone of the area postrema region of the brain. The anatomical site for this action of the benzamide derivatives, and whether such action is central (CNS), peripheral, or a combination thereof, remains unresolved (Barnes et al., J. Pharm. Pharmacol. 40: 586–588, 1988). Cisapride, like the other benzamide derivatives would appear to be an effective anti-emetic agent based on its ability to modulate the activity of serotonin at the $5HT_3$ receptor.

A second prominent action of the benzamide derivatives is in augmenting gastrointestinal smooth muscle activity from the esophagus through the proximal small bowel, thus accelerating esophageal and small intestinal transit as well as facilitating gastric emptying and increasing lower esophageal sphincter tone (Decktor et al., Eur. J. Pharmacol. 147: 313–316, 1988). Although the benzamide derivatives are not cholinergic receptor agonists per se, the aforementioned smooth muscle effects may be blocked by muscarinic receptor blocking agents such as atropine or neuronal transmission inhibitors of the tetrodotoxin type which affect sodium channels. Similar blocking activity has been reported for the contractile effects of serotonin in the small intestine. It is currently believed that the primary smooth muscle effects of the benzamide derivatives are the result of an agonist action upon a new class of serotonin receptors referred to as $5HT_4$ receptors which are located on interneurons in the myenteric plexus of the gut wall. Activation of these receptors subsequently enhances the release of acetylcholine from parasympathetic nerve terminals located near surrounding smooth muscle fibers, and it is the combination of acetylcholine with its receptors on smooth muscle membranes which is the actual trigger for muscle contraction.

A discussion of various 5HT receptors, including the $5HT_4$ receptor can be found in, for example, U.S. Pat. Nos. 6,331,401 and 6,632,827, which are incorporated by reference herein in their entirety.

Cisapride has been used primarily to treat gastroesophageal reflux disease (GERD). This disease is characterized as the backward flow of the stomach contents into the esophagus. One of the most important factors in the pathogenesis of gastroesophageal reflux disease is a reduction in the pressure barrier due to the failure of the lower esophageal sphincter. Failure of the lower esophageal sphincter can arise due to a low basal pressure, sphincter relaxation, or to a non-compensated increase in intragastric pressure. Other factors in the pathogenesis of the disease are delayed gastric emptying, insufficient esophageal clearing due to impaired peristalsis and the corrosive nature of the reflux material which can damage esophageal mucosa. Cisapride is thought to strengthen the anti-reflux barrier and improve esophageal clearance by increasing the lower esophageal sphincter pressure and enhancing peristaltic contractions.

Because of its activity as a prokinetic agent, cisapride would also appear to be useful to treat dyspepsia, gastroparesis, constipation, post-operative ileus, and intestinal pseudo-obstruction. Dyspepsia is a condition characterized by an impairment of the power or function of digestion that can arise as a symptom of a primary gastrointestinal dysfunction or as a complication due to other disorders such as appendicitis, gallbladder disturbances, or malnutrition. Gastroparesis is a paralysis of the stomach brought about by a motor abnormality in the stomach or as a complication of diseases such as diabetes, progressive systemic sclerosis, anorexia nervosa or myotonic dystrophy. Constipation is a condition characterized by infrequent or difficult evacuation of feces resulting from conditions such as lack of intestinal muscle tone or intestinal spasticity. Post-operative ileus is an obstruction in the intestine due to a disruption in muscle tone following surgery. Intestinal pseudo-obstruction is a condition characterized by constipation, colicky pain, and vomiting, but without evidence of physical obstruction.

Drug toxicity is an important consideration in the treatment of humans and animals. Toxic side effects (adverse effects) resulting from the administration of drugs include a variety of conditions which range from low grade fever to death. Drug therapy is justified only when the benefits of the treatment protocol outweigh the potential risks associated with the treatment. The factors balanced by the practitioner include the qualitative and quantitative impact of the drug to be used as well as the resulting outcome if the drug is not provided to the individual. Other factors considered include the physical condition of the patient, the disease stage and its history of progression, and any known adverse effects associated with a drug.

Drug elimination is typically the result of metabolic activity upon the drug and the subsequent excretion of the drug from the body. Metabolic activity can take place within the vascular supply and/or within cellular compartments or organs. The liver is a principal site of drug metabolism. The metabolic process can be categorized into synthetic and nonsynthetic reactions. In nonsynthetic reactions, the drug is chemically altered by oxidation, reduction, hydrolysis, or any combination of the aforementioned processes. These processes are collectively referred to as Phase I reactions.

In Phase II reactions, also known as synthetic reactions or conjugations, the parent drug, or intermediate metabolites thereof, are combined with endogenous substrates to yield an addition or conjugation product. Metabolites formed in synthetic reactions are, typically, more polar and biologically inactive. As a result, these metabolites are more easily excreted via the kidneys (in urine) or the liver (in bile). Synthetic reactions include glucuronidation, amino acid conjugation, acetylation, sulfoconjugation, and methylation.

More than 90% of a dose of cisapride is metabolized by oxidative N-dealkylation at the piperidine nitrogen or by aromatic hydroxylation occurring on either the 4-fluorophenoxy or benzamide rings.

The administration of cisapride to a human has been found to cause serious adverse effects including CNS disorders, increased systolic pressure, interactions with other drugs, diarrhea, and abdominal cramping. Further, it has been reported that intravenous administration of cisapride demonstrates the occurrence of additional adverse effects not experienced after oral administration of cisapride (Stacher et al. [1987] Digestive Diseases and Sciences 32(11): 1223–1230). It is believed that these adverse effects are caused by the metabolites that result from the oxidative dealkylation or aromatic hydroxylation of the compound which occurs in the cytochrome P450 detoxification system. Cisapride is also subject to a number of undesirable drug/drug interactions that are also a result of metabolism by the cytochrome P450 system.

Between July 1993 and December 1999, cisapride (PROPULSID, Janssen Pharmaceutica Products, L.P.) was reportedly associated with at least 341 serious cardiac arrhythmias. These arrhythmias include ventricular tachycardia, ventricular fibrillation, torsades de pointes, and QT prolongation. Eighty (80) deaths have been reported. As a result of these adverse effects, the product was voluntarily withdrawn from the open market in the United States; however, the drug is available through an investigational limited access program.

The safety of 5HT$_4$ receptor agonists with gastrointestinal (GI) prokinetic activity has been limited due to cardiac effects (prolongation of QTc intervals, tachycardia, torsades de pointes) and adverse drug interactions due to hepatic cytochrome P-450 metabolism. A GI prokinetic agent of this class that lacks these liabilities would be very valuable in several therapeutic areas including GERD and gastric emptying disorders. Certain cisapride derivatives have been described in U.S. Pat. No. 6,552,046 and WO 01/093849 (incorporated by reference herein in their entireties), however further compounds with even more advantageous properties would be desirable.

It has now been discovered that certain stereoisomers of one such esterified structural and/or functional analog of cisapride have distinct and particularly advantageous properties.

BRIEF SUMMARY

The subject invention provides compounds and compositions of formula (X), which stereoisomeric esterified cisapride analogs, for the safe and effective treatment of various gastrointestinal disorders including, but not limited to, gastroparesis, gastroesophageal reflux and related conditions. The compounds of the subject invention are also useful in treating a variety of conditions involving the central nervous system.

The compounds of the invention comprise compounds of formula X:

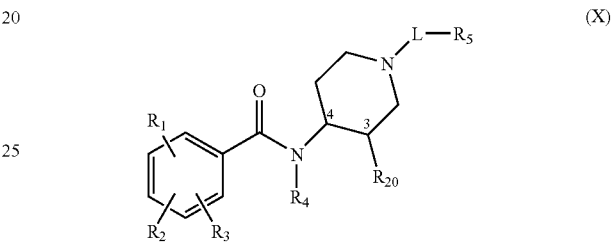

and pharmaceutically acceptable salts thereof, wherein
the bonds at positions 3 and 4 are cis relative to each other;

L is —($C_1$–$C_6$ alkyl)- (in one aspect, —($C_3$–$C_5$ alkyl)-), —($C_1$–$C_6$ alkyl)-C(O)—, or —C(O)—($C_1$–$C_6$ alkyl)-, wherein each of the alkyl groups is optionally substituted with 1 or 2 groups that are independently halogen, $C_1$–$C_4$ alkoxy, or OH and wherein one carbon in the alkyl portion of L may be replaced by —N($R_9$)—;

$R_1$ is halogen;

$R_2$ is amino, NH($C_1$–$C_4$ alkyl) or N($C_1$–$C_4$ alkyl)($C_1$–$C_4$ alkyl);

$R_3$ is OH or $C_1$–$C_4$ alkoxy;

$R_4$ is H or methyl; and $R_5$ is —O—$C_3$–$C_8$ cycloalkyl, —O-heterocycloalkyl, heterocycloalkyl, aryl, —O-aryl, —N($R_9$)—($C_0$–$C_6$ alkyl)-C(O)-aryl, or —N($R_9$)—$C_0$–$C_6$ alkyl-aryl, —O-heteroaryl, —N($R_9$)—$C_1$–$C_6$(O)-heteroaryl, or —N($R_9$)—$C_0$–$C_6$ alkyl-heteroaryl, wherein each of the cyclic groups is unsubstituted or substituted at one or more substitutable positions with $C_1$–$C_6$ alkyl, $C_1$–$C_6$ alkoxy, halogen, $C_1$–$C_6$ haloalkyl, $C_1$–$C_6$ haloalkoxy, hydroxyl, hydroxy-$C_1$–$C_4$-alkyl, amino, —NH($C_1$–$C_6$ alkyl), —N($C_1$–$C_6$ alkyl)($C_1$–$C_6$ alkyl), —($C_0$–$C_6$ alkyl)-C(O)$R_{11}$, or —O—($C_0$–$C_6$ alkyl)-C(O)$R_{11}$, methylsulfone, $C_0$–$C_6$-sulfonamide, or $NO_2$; wherein $R_9$ at each occurrence is independently H or $C_1$–$C_4$ alkyl;

$R_{11}$ is $C_1$–$C_6$ alkyl, OH, or $R_{11}$ is $C_1$–$C_6$ alkoxy, optionally substituted with 1 or 2 groups that are independently $C_1$–$C_4$ alkoxy, amino, —NH($C_1$–$C_6$ alkyl), —N($C_1$–$C_6$ alkyl)($C_1$–$C_6$ alkyl), —($C_0$–$C_6$ alkyl)-C(O)N($R_9$)-heterocycloalkyl, —O-heterocycloalkyl, —$C_1$–$C_6$(O)N($R_9$)-heteroaryl, or heteroaryl, wherein
the heterocycloalkyl groups are optionally substituted with 1, 2, or 3 groups that are independently halogen, $C_1$–$C_6$ alkyl, $C_1$–$C_6$ alkoxy, hydroxy, hydroxy $C_1$–$C_6$ alkyl, $C_1$–$C_6$ alkoxycarbonyl, —$CO_2$H, $CF_3$, or $OCF_3$, the heteroaryl group is optionally substituted with 1, 2, or 3 groups that are independently halogen, $C_1$–$C_6$ alkyl, $C_1$–$C_6$ alkoxy, hydroxy, hydroxy $C_1$–$C_6$ alkyl, $C_1$–$C_6$ alkoxycarbonyl, —$CO_2H$, $CF_3$, or $OCF_3$; or $R_{11}$ is —O-heterocycloalkyl wherein the heterocycloalkyl is optionally substituted with 1, 2, or 3 groups that are independently halogen, $C_1$–$C_6$ alkyl, $C_1$–$C_6$ alkoxy, hydroxy, hydroxy $C_1$–$C_6$ alkyl, $C_1$–$C_6$ alkoxycarbonyl, —$CO_2H$, $CF_3$, or $OCF_3$; and $R_{20}$ is $C_1$–$C_6$ alkoxy (preferably $C_1$–$C_4$ alkoxy, more preferably methoxy), or OH.

The invention also encompasses compositions comprising at least one compound of formula (X) and at least one pharmaceutically acceptable excipient, adjuvant, carrier, or solvent.

The compounds of formula (X) are useful in the treatment or prevention of gastroesophageal reflux disease and substantially reduce adverse effects associated with the administration of cisapride. These adverse effects include, but are not limited to, diarrhea, abdominal cramping and elevations of blood pressure and heart rate.

Additionally, the compounds and compositions of the invention are useful in treating emesis and other conditions, including but not limited to dyspepsia, gastroparesis, constipation, post-operative ileus and intestinal pseudo-obstruction. As an added benefit, adverse effects associated with the administration of cisapride are also reduced in these methods of treatment.

Advantageously, the compounds of the subject invention are ligands for the 5$HT_4$ receptor and, accordingly, can be used to treat conditions mediated through this receptor. These receptors are located in several areas of the central nervous system and the modulation of these receptors can be used to effect desired modulations of the CNS.

Advantageously, the subject invention provides stereoisomeric compounds which contain an ester moiety that does not detract from the ability of these compounds to provide a therapeutic benefit, but which makes them more susceptible to degradation by serum and/or cytosolic esterases, thereby avoiding the cytochrome P450 drug detoxification system associated with adverse effects caused by cisapride and reducing the incidence of such adverse events.

The subject invention further provides methods of treatment comprising the administration of the compounds of formula (X) and therapeutically effective amounts to individuals in need of treatment for gastroesophageal reflux disease, dyspepsia, gastroparesis, constipation, post-operative ileus, and intestinal pseudo-obstruction; and related conditions.

Advantageously, the therapeutic compounds of the subject invention are stable in storage and provide for safer metabolism of the drugs as compared to other drugs; therefore, the compounds of the subject invention can be used with a lower incidence of side effects and toxicity.

In a further aspect, the subject invention pertains to the breakdown products (preferably metabolic breakdown products) which are formed when the therapeutic compounds of the subject invention are acted upon by esterases. These breakdown products can be used as described herein to monitor the clearance of the therapeutic compounds from a patient.

In yet a further aspect, the subject invention provides methods for synthesizing the therapeutic stereoisomeric compounds of the subject invention, as well as intermediates useful in preparing the compounds of interest.

BRIEF DESCRIPTION OF THE DRAWINGS

FIG. 1 is a graph representing the Concentration-Response Curves for 5-$HT_4$ Receptor Agonism of ATI-7505, serotonin, Cisapride, and ATI-7500.

FIG. 2 is a graph representing gastric emptying in fed dogs. The data shown are normalized to the averaged vehicle control times of MMC return values. Values represent mean+SEM of 5 dogs. *$p<0.05$ versus vehicle controls.

FIG. 3 is a graph representing the metabolism of ATI-7505 and ATI-7500, with and without the CYP450 dependent Cofactor, NADPH. The plots show mean and SD μM concentrations of ATI-7505 and ATI-7500. ATI-7505 (2 μM) was incubated with human microsomal protein (1 mg) in the presence or absence of NADPH regenerating system (cofactor).

DETAILED DISCLOSURE

In a further aspect, the invention provides compounds of Formula (X), wherein $R_5$ is —O—$C_3$–$C_8$ cycloalkyl, —O-heterocycloalkyl, heterocycloalkyl, wherein the heterocycloalkyl group is selected from piperidinyl, piperazinyl, pyrrolidinyl, aza-bicyclo-octyl, in certain embodiments aza-bicyclo[2.2.2]octyl, aza-bicyclo[3.2.1]octyl, aza-bicyclo-nonyl, aza-bicyclo-decyl, indolinyl, morpholinyl, thiomorpholinyl, S,S-dioxothiomorpholinyl, and imidazolidinyl, —O-aryl, —N($R_9$)—C(O)-aryl, or —N($R_9$)—$C_0$–$C_6$ alkyl-aryl, wherein each of the cyclic groups is unsubstituted or substituted at one or more substitutable positions with $C_1$–$C_6$ alkyl, $C_1$–$C_6$ alkoxy, halogen, $C_1$–$C_6$ haloalkyl, $C_1$–$C_6$ haloalkoxy, hydroxyl, hydroxy-$C_1$–$C_4$-alkyl, amino, —NH($C_1$–$C_6$ alkyl), —N($C_1$–$C_6$ alkyl)($C_1$–$C_6$ alkyl), —C(O)$R_{11}$, or $NO_2$; wherein $R_9$ at each occurrence is independently H or $C_1$–$C_4$ alkyl; and $R_{11}$ is $C_1$–$C_6$ alkyl, OH, or $R_{11}$ is $C_1$–$C_6$ alkoxy, optionally substituted with 1 or 2 groups that are independently $C_1$–$C_4$ alkoxy, amino, —NH($C_1$–$C_6$ alkyl), —N($C_1$–$C_6$ alkyl)($C_1$–$C_6$ alkyl), —C(O)N($R_9$)-heterocycloalkyl, heterocycloalkyl or heteroaryl, wherein the heterocycloalkyl group is selected from pyrrolidinyl, piperidinyl, piperazinyl, morpholinyl, aza-bicyclo-octyl, in certain embodiments aza-bicyclo[2.2.2]octyl, aza-bicyclo[3.2.1]octyl, aza-bicyclo-nonyl and aza-bicyclo-decyl, wherein the heterocycloalkyl groups are optionally substituted with 1, 2, or 3 groups that are independently halogen, $C_1$–$C_6$ alkyl, $C_1$–$C_6$ alkoxy, hydroxy, hydroxy $C_1$–$C_6$ alkyl, $C_1$–$C_6$ alkoxycarbonyl, —$CO_2H$, $CF_3$, or $OCF_3$, the heteroaryl group is selected from pyridyl, pyrimidyl, quinolinyl, isoquinolinyl, and indolyl, wherein the heteroaryl groups are optionally substituted with 1, 2, or 3 groups that are independently halogen, $C_1$–$C_6$ alkyl, $C_1$–$C_6$ alkoxy, hydroxy, hydroxy $C_1$–$C_6$ alkyl, $C_1$–$C_6$ alkoxycarbonyl, —$CO_2H$, $CF_3$, or $OCF_3$; or $R_{11}$ is —O-heterocycloalkyl wherein the heterocycloalkyl is selected from piperidinyl, pyrrolidinyl, imidazolidinyl, morpholinyl, aza-bicyclo-octyl, in certain embodiments aza-bicyclo[2.2.2]octyl, aza-bicyclo[3.2.1]octyl, aza-bicyclo-nonyl, aza-bicyclo-decyl, and tetrahydrofuranyl, and wherein each heterocycloalkyl group is optionally substituted with 1, 2, or 3 groups that are independently halogen, $C_1$–$C_6$ alkyl, $C_1$–$C_6$ alkoxy, hydroxy, hydroxy $C_1$–$C_6$ alkyl, $C_1$–$C_6$ alkoxycarbonyl, —$CO_2H$, $CF_3$, or $OCF_3$.

In another aspect, the invention provides compounds of Formula (X), wherein $R_1$ is chloro.

In yet another aspect, the invention provides compounds of Formula (X), wherein $R_2$ is amino.

In still another aspect, the invention provides compounds of Formula (X), wherein $R_3$ is methoxy.

In another aspect, the invention provides compounds of Formula (X), wherein $R_4$ is H or methyl.

In still yet another aspect, the invention provides compounds of Formula (X), wherein $R_1$ is chloro; $R_2$ is amino; $R_3$ is methoxy; and $R_4$ is H or methyl.

In yet another aspect, the invention provides compounds of Formula (X), wherein $R_1$ is chloro; $R_2$ is amino; $R_3$ is methoxy; $R_4$ is H, and L is —($C_4$–$C_6$ alkyl)-C(O)—.

In another aspect, the invention provides compounds of formula (X), wherein two or more previously described aspects are combined.

In another aspect, the invention provides compounds of Formula (XI), which are compounds of formula (X) wherein L is —(CH$_2$)$_5$—C(O)—:

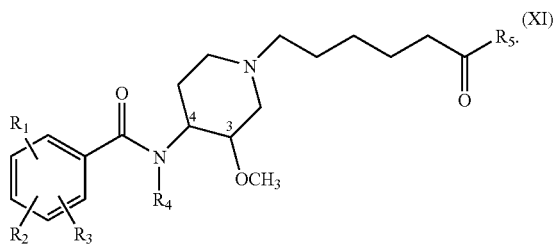

In yet still another aspect, the invention provides compounds of formula (XI), wherein $R_1$ is chloro; $R_2$ is amino; $R_3$ is methoxy; and $R_4$ is H or methyl.

In still another aspect, the invention provides compounds of formula (XI), wherein $R_5$ is —O-heterocycloalkyl, wherein the heterocycloalkyl group is selected from aza-bicyclo-octyl, in certain embodiments 1-aza-bicyclo[2.2.2]oct-3-yl or 8-aza-bicyclo[3.2.1]oct-3-yl, aza-bicyclo-nonyl, aza-bicyclo-decyl, where the aza nitrogen, is optionally substituted with methyl or ethyl; and $R_4$ is H or methyl.

In still yet another aspect, the invention provides compounds of formula (XI), wherein $R_5$ is —O-heterocycloalkyl, wherein the heterocycloalkyl group is selected from piperidinyl, piperazinyl, or pyrrolidinyl, each of which is unsubstituted or substituted at one or two positions with groups that are independently $C_1$–$C_4$ alkyl, $C_1$–$C_4$ alkoxy, halogen, $C_1$–$C_4$ haloalkyl (in one aspect, $CF_3$), $C_1$–$C_4$ haloalkoxy (in one aspect $OCF_3$), hydroxyl, hydroxy $C_1$–$C_4$ alkyl, amino, —NH($C_1$–$C_4$ alkyl), —N($C_1$–$C_4$ alkyl)($C_1$–$C_4$ alkyl), —($C_1$–$C_6$ alkyl)-C(O)$R_{11}$, or $NO_2$; and $R_4$ is H or methyl.

In yet another aspect, the invention provides compounds of formula (XI), wherein $R_5$ is —O-heterocycloalkyl, wherein the heterocycloalkyl group is selected from indolinyl, morpholinyl, thiomorpholinyl, S,S-dioxothiomorpholinyl, and imidazolidinyl, each of which is unsubstituted or substituted at one or two positions with groups that are independently $C_1$–$C_4$ alkyl, $C_1$–$C_4$ alkoxy, halogen, $C_1$–$C_4$ haloalkyl (in one aspect, $CF_3$), $C_1$–$C_4$ haloalkoxy (in one aspect $OCF_3$), hydroxyl, hydroxy $C_1$–$C_4$ alkyl, amino, —NH($C_1$–$C_4$ alkyl), —N($C_1$–$C_4$ alkyl)($C_1$–$C_4$ alkyl), —($C_0$–$C_6$ alkyl)-C(O)$R_{11}$, or $NO_2$; and $R_4$ is H or methyl.

In yet another aspect, the invention provides compounds of formula (XI), wherein $R_5$ is —O-phenyl, N($R_9$)—($C_0$–$C_6$ alkyl)-C(O)-phenyl, or —N($R_9$)—$C_0$–$C_4$ alkyl-phenyl, wherein the phenyl group is substituted with one or two groups that are independently $C_1$–$C_4$ alkyl, $C_1$–$C_4$ alkoxy, halogen, $C_1$–$C_4$ haloalkyl (in one aspect, $CF_3$), $C_1$–$C_4$ haloalkoxy (in one aspect $OCF_3$), hydroxyl, hydroxy $C_1$–$C_4$ alkyl, amino, —NH($C_1$–$C_4$ alkyl), —N($C_1$–$C_4$ alkyl)($C_1$–$C_4$ alkyl), —($C_0$–$C_6$ alkyl)-C(O)$R_{11}$, or $NO_2$; and $R_4$ and $R_9$ are independently H or methyl.

In another aspect, the invention provides compounds of formula (XI), wherein $R_4$ is H.

In yet another aspect, the invention provides compounds of formula (XI), wherein $R_{11}$ is $C_1$–$C_6$ alkoxy, optionally substituted with 1 or 2 groups that are independently $C_1$–$C_4$ alkoxy, amino, —NH($C_1$–$C_6$ alkyl), —N($C_1$–$C_6$ alkyl)($C_1$–$C_6$ alkyl), —($C_0$–$C_6$ alkyl)-C(O)N($R_9$)-heterocycloalkyl, or heterocycloalkyl wherein the heterocycloalkyl group is selected from pyrrolidinyl, piperidinyl, piperazinyl, and morpholinyl, wherein the heterocycloalkyl groups are optionally substituted with 1, 2, or 3 groups that are independently halogen, $C_1$–$C_6$ alkyl, $C_1$–$C_6$ alkoxy, hydroxy, hydroxy $C_1$–$C_6$ alkyl, $C_1$–$C_6$ alkoxycarbonyl, —$CO_2H$, $CF_3$, or $OCF_3$.

In another aspect, the invention provides compounds of formula (XI), wherein two or more previously described aspects are combined.

In another aspect, the invention provides compounds of Formula (XII), i.e., compounds of formula (X), of the formula:

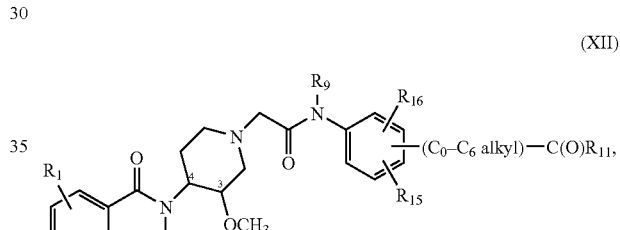

wherein $R_{15}$ is H, $C_1$–$C_6$ alkyl, $C_1$–$C_6$ alkoxy, halogen, $C_1$–$C_6$ haloalkyl (in one aspect $CF_3$), $C_1$–$C_6$ haloalkoxy (in one aspect $OCF_3$), hydroxyl, hydroxy $C_1$–$C_4$ alkyl, amino, —NH($C_1$–$C_6$ alkyl), —N($C_1$–$C_6$ alkyl)($C_1$–$C_6$ alkyl), methylsulfone, $C_0$–$C_6$-sulfonamide or $NO_2$, and $R_{16}$ is H or —O—($C_0$–$C_6$ alkyl)-C(O)$R_{11}$. In another aspect, $R_{15}$ is H.

In yet another aspect, the invention provides compounds of formula (XII), wherein $R_4$ and $R_9$ are independently H or methyl and $R_{11}$ is OH.

In still yet another aspect, the invention provides compounds of formula (XII), wherein $R_4$ and $R_9$ are independently H or methyl and $R_{11}$ is $C_1$–$C_6$ alkoxy, optionally substituted with 1 or 2 groups that are independently $C_1$–$C_4$ alkoxy, amino, —NH($C_1$–$C_6$ alkyl), —N($C_1$–$C_6$ alkyl)($C_1$–$C_6$ alkyl), —($C_0$–$C_6$ alkyl)-C(O)N($R_9$)-heterocycloalkyl, or heterocycloalkyl wherein the heterocycloalkyl group is selected from aza-bicyclo-octyl, in certain embodiments 1-aza-bicyclo[2.2.2]oct-3-yl or 8-aza-bicyclo[3.2.1]oct-3-yl, aza-bicyclo-nonyl, aza-bicyclo-decyl, where the aza nitrogen is optionally substituted with methyl or ethyl, pyrrolidinyl, piperidinyl, piperazinyl, and morpholinyl, wherein the heterocycloalkyl groups are optionally substituted with 1, 2, or 3 groups that are independently halogen, $C_1$–$C_6$ alkyl, $C_1$–$C_6$ alkoxy, hydroxy, hydroxy $C_1$–$C_6$ alkyl, $C_1$–$C_6$ alkoxycarbonyl, —$CO_2H$, $CF_3$, or $OCF_3$, and $R_4$ and $R_9$ are independently H or methyl. In another aspect, $R_4$, $R_9$, and $R_{11}$ are as previously defined and $R_{15}$ is H, $R_1$ is chloro; $R_2$ is amino; and $R_3$ is methoxy.

In yet still another aspect, the invention provides compounds of formula (XII), wherein $R_4$ and $R_9$ are independently H or methyl and $R_{11}$ is $C_1$–$C_6$ alkoxy, optionally substituted with 1 or 2 groups that are independently $C_1$–$C_4$ alkoxy, amino, —NH($C_1$–$C_6$ alkyl), —N($C_1$–$C_6$ alkyl)($C_1$–$C_6$ alkyl), or heteroaryl, wherein the heteroaryl group is selected from pyridyl, pyrimidyl, quinolinyl, isoquinolinyl, and indolyl, wherein the heteroaryl groups are optionally substituted with 1, 2, or 3 groups that are independently halogen, $C_1$–$C_6$ alkyl, $C_1$–$C_6$ alkoxy, hydroxy, hydroxy $C_1$–$C_6$ alkyl, $C_1$–$C_6$ alkoxycarbonyl, —$CO_2$H, $CF_3$, or $OCF_3$; and $R_4$ and $R_9$ are independently H or methyl. In another aspect, $R_4$, $R_9$, and $R_{11}$ are as previously defined and $R_{15}$ is H, $R_1$ is chloro; $R_2$ is amino; and $R_3$ is methoxy.

In still another aspect, the invention provides compounds of formula (XII), wherein at least one of $R_4$ and $R_9$ is H.

In another aspect, the invention provides compounds of formula (XII), wherein two or more previously described aspects are combined.

In another aspect, the invention provides compounds of Formula (XIII), i.e., compounds of formula (XII), of the formula:

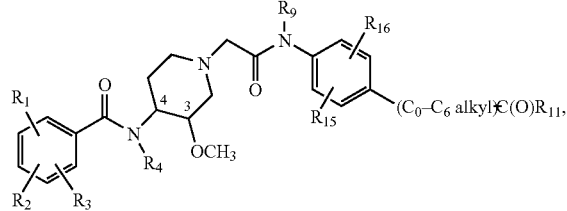

(XIII)

wherein $R_{15}$ is H, $C_1$–$C_6$ alkyl, $C_1$–$C_6$ alkoxy, halogen, $C_1$–$C_6$ haloalkyl (in one aspect $CF_3$), $C_1$–$C_6$ haloalkoxy (in one aspect $OCF_3$), hydroxyl, hydroxy $C_1$–$C_4$ alkyl, amino, —NH($C_1$–$C_6$ alkyl), —N($C_1$–$C_6$ alkyl)($C_1$–$C_6$ alkyl), or methylsulfone, $C_0$–$C_6$-sulfonamide, $NO_2$, and $R_{16}$ is H or —O—($C_0$–$C_6$ alkyl)-C(O)$R_{11}$. In another aspect, $R_{15}$ is H.

In yet another aspect, the invention provides compounds of formula (XIII), wherein $R_4$ and $R_9$ are independently H or methyl, and $R_{11}$ is OH, $C_1$–$C_4$ alkoxy (in another aspect, $C_1$–$C_3$ alkoxy), or $C_1$–$C_2$ alkoxy-$C_1$–$C_3$ alkoxy-. In another aspect, $R_4$, $R_9$, and $R_{11}$, are as previously defined and $R_1$ is chloro; $R_2$ is amino; and $R_3$ is methoxy.

In still yet another aspect, the invention provides compounds of formula (XIII), wherein $R_4$ and $R_9$ are independently H or methyl, and $R_{11}$ is $C_1$–$C_4$ alkoxy substituted with amino, —NH($C_1$–$C_6$ alkyl), —N($C_1$–$C_6$ alkyl)($C_1$–$C_6$ alkyl), aza-bicyclo-octyl, in certain embodiments 1-aza-bicyclo[2.2.2]oct-3-yl or 8-aza-bicyclo[3.2.1]oct-3-yl, aza-bicyclo-nonyl, aza-bicyclo-decyl, where the aza nitrogen is optionally substituted with methyl or ethyl; and $R_4$ is H or methyl, pyrrolidinyl, piperidinyl, morpholinyl, pyridyl, or —($C_0$–$C_6$ alkyl)-C(O)NH-pyrid-4-yl. In another aspect, $R_4$, $R_9$, and $R_{11}$ are as previously defined and $R_1$ is chloro; $R_2$ is amino; and $R_3$ is methoxy.

In still another aspect, the invention provides compounds of formula (XIII), wherein $R_4$ and $R_9$ are independently H or methyl, and $R_{11}$ is $C_1$–$C_4$ alkoxy substituted with amino, —NH($C_1$–$C_6$ alkyl), or —N($C_1$–$C_6$ alkyl)($C_1$–$C_6$ alkyl). In another aspect, $R_4$, $R_9$, and $R_{11}$, are as previously defined and $R_1$ is chloro; $R_2$ is amino; and $R_3$ is methoxy.

In yet another aspect, the invention provides compounds of formula (XIII), wherein $R_4$ and $R_9$ are independently H or methyl, and $R_{11}$ is $C_1$–$C_4$ alkoxy substituted with pyrrolidinyl, piperidinyl, morpholinyl, pyridyl, or —($C_0$–$C_6$ alkyl)-C(O)NH-pyrid-4-yl. In another aspect, $R_4$, $R_9$, and $R_{11}$ are as previously defined and $R_1$ is chloro; $R_2$ is amino; and $R_3$ is methoxy.

In still another aspect, the invention provides compounds of formula (XIII), wherein at least one of $R_4$ and $R_9$ is H.

In another aspect, the invention provides compounds of formula (XIII), wherein two or more previously described aspects are combined.

In another aspect, the invention provides compounds of formula (XIV), i.e., compounds of formula (X), of the formula:

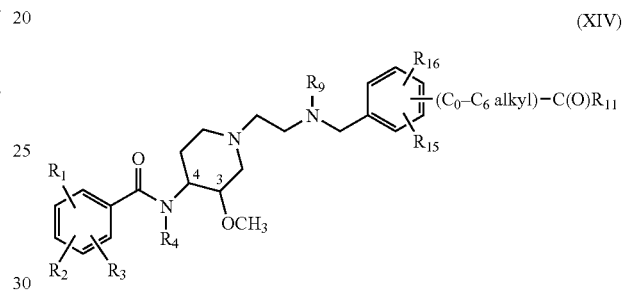

(XIV)

wherein $R_{15}$ is H, $C_1$–$C_6$ alkyl, $C_1$–$C_6$ alkoxy, halogen, $C_1$–$C_6$ haloalkyl (in one aspect $CF_3$), $C_1$–$C_6$ haloalkoxy (in one aspect $OCF_3$), hydroxyl, hydroxy $C_1$–$C_4$ alkyl, amino, —NH($C_1$–$C_6$ alkyl), —N($C_1$–$C_6$ alkyl)($C_1$–$C_6$ alkyl), methylsulfone, $C_0$–$C_6$-sulfonamide, or $NO_2$, and $R_{16}$ is H or —O—($C_0$–$C_6$ alkyl)-C(O)$R_{11}$. In another aspect, $R_{15}$ is H.

In still another aspect, the invention provides compounds of formula (XIV), wherein $R_4$ and $R_9$ are independently H or methyl, and $R_{11}$ is OH, $C_1$–$C_4$ alkoxy (in another aspect, $C_1$–$C_3$ alkoxy) or $C_1$–$C_2$ alkoxy-$C_1$–$C_3$ alkoxy-. In another aspect, $R_4$, $R_9$, and $R_{11}$ are as previously defined and $R_1$ is chloro; $R_2$ is amino; and $R_3$ is methoxy. In still another aspect, at least one of $R_4$ and $R_9$ is H.

In yet still another aspect, the invention provides compounds of formula (XIV), wherein $R_4$ and $R_9$ are independently H or methyl, and $R_{11}$ is $C_1$–$C_4$ alkoxy substituted with amino, —NH($C_1$–$C_6$ alkyl), —N($C_1$–$C_6$ alkyl)($C_1$–$C_6$ alkyl), aza-bicyclo-octyl, in certain embodiments 1-aza-bicyclo[2.2.2]oct-3-yl or 8-aza-bicyclo[3.2.1]oct-3-yl, aza-bicyclo-nonyl, aza-bicyclo-decyl, where the aza nitrogen is optionally substituted with methyl or ethyl; and $R_4$ is H or methyl, pyrrolidinyl, piperidinyl, morpholinyl, pyridyl, or —($C_0$–$C_6$ alkyl)-C(O)NH-pyrid-4-yl. In another aspect, $R_4$, $R_9$, and $R_{11}$ are as previously defined and $R_1$ is chloro; $R_2$ is amino; and $R_3$ is methoxy.

In still another aspect, the invention provides compounds of formula (XIV), wherein $R_4$ and $R_9$ are independently H or methyl, and $R_{11}$ is $C_1$–$C_4$ alkoxy substituted with amino, —NH($C_1$–$C_6$ alkyl), or —N($C_1$–$C_6$ alkyl)($C_1$–$C_6$ alkyl). In another aspect, $R_4$, $R_9$, and $R_{11}$ are as previously defined and $R_1$ is chloro; $R_2$ is amino; and $R_3$ is methoxy.

In yet another aspect, the invention provides compounds of formula (XIV), wherein $R_4$ and $R_9$ are independently H or methyl, and $R_{11}$ is $C_1$–$C_4$ alkoxy substituted with pyrrolidinyl, piperidinyl, morpholinyl, pyridyl, or —($C_0$–$C_6$ alkyl)-

C(O)NH-pyrid-4-yl. In another aspect, $R_4$, $R_9$, and $R_{11}$ are as previously defined and $R_1$ is chloro; $R_2$ is amino; and $R_3$ is methoxy.

In still another aspect, the invention provides compounds of formula (XIV), wherein at least one of $R_4$ and $R_9$ is H.

In another aspect, the invention provides compounds of formula (XIV), wherein two or more previously described aspects are combined.

In another aspect, the invention provides compounds of formula (XV), i.e., compounds of formula (X) of the formula:

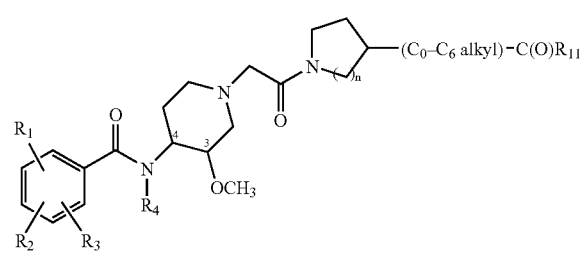

(XV)

wherein n is 1 or 2.

In still another aspect, the invention provides compounds of formula (XV), wherein $R_4$ is H or methyl, and $R_{11}$ is OH, $C_1-C_4$ alkoxy (in another aspect, $C_1-C_3$ alkoxy) or $C_1-C_2$ alkoxy-$C_1-C_3$ alkoxy-. In another aspect, $R_4$ and $R_{11}$ are as previously defined and $R_1$ is chloro; $R_2$ is amino; and $R_3$ is methoxy. In still another aspect, at least one of $R_4$ and $R_9$ is H.

In yet still another aspect, the invention provides compounds of formula (XV), wherein $R_4$ and $R_9$ are independently H or methyl, and $R_{11}$ is $C_1-C_4$ alkoxy substituted with amino, —NH($C_1-C_6$ alkyl), —N($C_1-C_6$ alkyl)($C_1-C_6$ alkyl), aza-bicyclo-octyl, in certain embodiments 1-aza-bicyclo[2.2.2]oct-3-yl or 8-aza-bicyclo[3.2.1]oct-3-yl, aza-bicyclo-nonyl, aza-bicyclo-decyl, where the aza nitrogen is optionally substituted with methyl or ethyl; and $R_4$ is H or methyl, pyrrolidinyl, piperidinyl, morpholinyl, pyridyl, or —C(O)NH-pyrid-4-yl. In another aspect, $R_4$, $R_9$, and $R_{11}$ are as previously defined and $R_1$ is chloro; $R_2$ is amino; and $R_3$ is methoxy.

In still another aspect, the invention provides compounds of formula (XV), wherein $R_4$ and $R_9$ are independently H or methyl, and $R_{11}$ is $C_1-C_4$ alkoxy substituted with amino, —NH($C_1-C_6$ alkyl), or —N($C_1-C_6$ alkyl)($C_1-C_6$ alkyl). In another aspect, $R_4$, $R_9$, and $R_{11}$ are as previously defined and $R_1$ is chloro; $R_2$ is amino; and $R_3$ is methoxy.

In yet another aspect, the invention provides compounds of formula (XV), wherein $R_4$ is H or methyl, and $R_{11}$ is $C_1-C_4$ alkoxy substituted with aza-bicyclo-octyl, in certain embodiments 1-aza-bicyclo[2.2.2]oct-3-yl or 8-aza-bicyclo[3.2.1]oct-3-yl, aza-bicyclo-nonyl, aza-bicyclo-decyl, where the aza nitrogen is optionally substituted with methyl or ethyl; and $R_4$ is H or methyl, pyrrolidinyl, piperidinyl, morpholinyl, pyridyl, or —($C_0-C_6$ alkyl)-C(O)NH-pyrid-4-yl. In another aspect, $R_4$, $R_9$, and $R_{11}$ are as previously defined and $R_1$ is chloro; $R_2$ is amino; and $R_3$ is methoxy.

In another aspect, the invention provides compounds of formula (XV), wherein two or more previously described aspects are combined.

In another aspect, the invention provides compounds according to any one of formulas (X), (XI), (XII), (XIII), (XIV) or (XV), wherein $R_1$, $R_2$, and $R_3$ are oriented on the phenyl ring as follows:

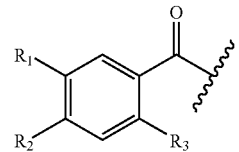

In another aspect, the invention provides compounds according to any one of formulas (X), (XI), (XII), (XIII), (XIV) or (XV), wherein bond 3 has the "S" configuration and bond 4 has the "R" configuration.

In still another aspect, the invention provides compounds according to any one of formulas (X), (XI), (XII), (XIII), (XIV) or (XV), wherein $R_1$, $R_2$, and $R_3$ are oriented on the phenyl ring as follows:

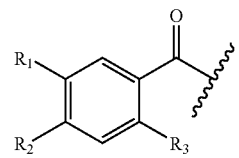

and bond 3 has the "S" configuration and bond 4 has the "R" configuration.

In another aspect, the invention provides compounds according to any one of formulas (X), (XI), (XII), (XIII), (XIV) or (XV), wherein bond 3 has the "R" configuration and bond 4 has the "S" configuration.

In another aspect, the invention provides compounds according to any one of formulas (X), (XI), (XII), (XIII), (XIV) or (XV), wherein $R_1$, $R_2$, and $R_3$ are oriented on the phenyl ring as follows:

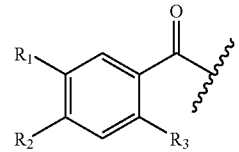

and bond 3 has the "R" configuration and bond 4 has the "S" configuration.

In still another aspect, the invention provides compounds of formula (X), wherein $R_1$ is chloro; $R_2$ is amino; $R_3$ is methoxy; $R_4$ is H, and $R_1$, $R_2$, and $R_3$ have the following orientation on the phenyl ring:

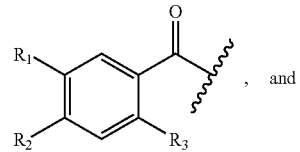

, and

L is —($C_3$–$C_5$ alkyl)- wherein one carbon may be replaced by —N($R_9$)—, or —($C_2$–$C_6$ alkyl)-C(O)—. In yet another aspect, the R1, R2, and R3 are as defined and oriented on the phenyl ring as previously described, $R_4$ is as previously defined and $R_5$ is —O-heterocycloalkyl, wherein the heterocycloalkyl group is selected from aza-bicyclo-octyl, in certain embodiments 1-aza-bicyclo[2.2.2]oct-3-yl or 8-aza-bicyclo[3.2.1]oct-3-yl, aza-bicyclo-nonyl, aza-bicyclo-decyl, where the aza nitrogen is optionally substituted with methyl or ethyl, piperidinyl, piperazinyl, and pyrrolidinyl, wherein the piperidinyl, piperazinyl, and pyrrolidinyl groups are unsubstituted or substituted at one or two positions with groups that are independently $C_1$–$C_4$ alkyl, $C_1$–$C_4$ alkoxy, halogen, $C_1$–$C_4$ haloalkyl, $C_1$–$C_4$ haloalkoxy, hydroxyl, hydroxy $C_1$–$C_4$ alkyl, amino, —NH($C_1$–$C_4$ alkyl), —N($C_1$–$C_4$ alkyl)($C_1$–$C_4$ alkyl), —($C_0$–$C_6$ alkyl)-C(O)$R_{11}$, or $NO_2$, wherein $R_{11}$ is $C_1$–$C_6$ alkoxy, optionally substituted with 1 or 2 groups that are independently $C_1$–$C_4$ alkoxy, amino, —NH ($C_1$–$C_6$ alkyl), —N($C_1$–$C_6$ alkyl)($C_1$–$C_6$ alkyl), —($C_0$–$C_6$ alkyl)-C(O)N($R_9$)-heterocycloalkyl, or heterocycloalkyl wherein the heterocycloalkyl group is selected from aza-bicyclo-octyl, in certain embodiments 1-aza-bicyclo[2.2.2] oct-3-yl or 8-aza-bicyclo[3.2.1]oct-3-yl, aza-bicyclo-nonyl, aza-bicyclo-decyl, where the aza nitrogen is optionally substituted with methyl or ethyl; and $R_4$ is H or methyl, pyrrolidinyl, piperidinyl, piperazinyl, and morpholinyl, wherein the heterocycloalkyl groups are optionally substituted with 1, 2, or 3 groups that are independently halogen, $C_1$–$C_6$ alkyl, $C_1$–$C_6$ alkoxy, hydroxy, hydroxy $C_1$–$C_6$ alkyl, $C_1$–$C_6$ alkoxycarbonyl, —$CO_2H$, $CF_3$, or $OCF_3$.

In still yet another aspect, the invention provides compounds of formula (X), wherein $R_1$ is chloro; $R_2$ is amino; $R_3$ is methoxy; $R_4$ is H, and $R_1$, $R_2$, and $R_3$ have the following orientation on the phenyl ring:

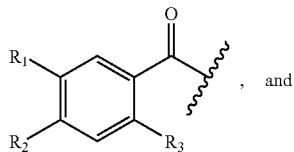

, and

L is —($C_3$–$C_5$ alkyl)- wherein one carbon may be replaced by —N($R_9$)—, or —($C_2$–$C_6$ alkyl)-C(O)—. In yet another aspect, the $R_1$, $R_2$, and $R_3$ are as defined and oriented on the phenyl ring as previously described, $R_4$ is as previously defined and $R_5$ is heterocycloalkyl, which is selected from aza-bicyclo-octyl, in certain embodiments 1-aza-bicyclo[2.2.2]oct-3-yl or 8-aza-bicyclo[3.2.1]oct-3-yl, aza-bicyclo-nonyl, aza-bicyclo-decyl, where the aza nitrogen is optionally substituted with methyl or ethyl.

In still yet another aspect, the invention provides compounds of formula (X), wherein $R_1$ is chloro; $R_2$ is amino; $R_3$ is methoxy; $R_4$ is H, and $R_1$, $R_2$, and $R_3$ have the following orientation on the phenyl ring:

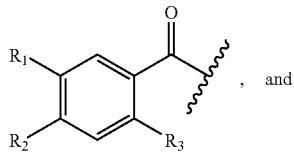

, and

L is —($C_3$–$C_5$ alkyl)- wherein one carbon may be replaced by —N($R_9$)—, or —($C_2$–$C_6$ alkyl)-C(O)—. In yet another aspect, the $R_1$, $R_2$, and $R_3$ are as defined and oriented on the phenyl ring as previously described, $R_4$ is as previously defined and $R_5$ is —N($R_9$)—CO—$C_4$ alkyl-aryl or —N($R_9$)—($C_0$–$C_6$ alkyl)-C(O)-aryl, wherein the aryl group is unsubstituted or substituted at one or more substitutable positions with $C_1$–$C_6$ alkyl, $C_1$–$C_6$ alkoxy, halogen, $C_1$–$C_6$ haloalkyl, $C_1$–$C_6$ haloalkoxy, hydroxyl, hydroxyalkyl, amino, —NH($C_1$–$C_6$ alkyl), —N($C_1$–$C_6$ alkyl)($C_1$–$C_6$ alkyl), —($C_0$–$C_6$ alkyl)-C(O)$R_{11}$, or $NO_2$. In still another aspect, the aryl group is a phenyl substituted with —($C_0$–$C_6$ alkyl)-C(O)$R_{11}$ and optionally substituted with 1 or 2 groups independently selected from $C_1$–$C_6$ alkyl, $C_1$–$C_6$ alkoxy, halogen, $CF_3$, $OCF_3$, hydroxyl, hydroxyalkyl, amino, —NH($C_1$–$C_4$ alkyl), —N($C_1$–$C_4$ alkyl)($C_1$–$C_4$ alkyl), or $NO_2$, wherein $R_{11}$ is $C_1$–$C_6$ alkoxy, optionally substituted with 1 or 2 groups that are independently $C_1$–$C_4$ alkoxy, amino, —NH ($C_1$–$C_6$ alkyl), —N($C_1$–$C_6$ alkyl)($C_1$–$C_6$ alkyl), —($C_0$–$C_6$ alkyl)-C(O)N($R_9$)-heterocycloalkyl, or heterocycloalkyl wherein the heterocycloalkyl group is selected from pyrrolidinyl, piperidinyl, piperazinyl, and morpholinyl, wherein the heterocycloalkyl groups are optionally substituted with 1, 2, or 3 groups that are independently halogen, $C_1$–$C_6$ alkyl, $C_1$–$C_6$ alkoxy, hydroxy, hydroxy $C_1$–$C_6$ alkyl, $C_1$–$C_6$ alkoxycarbonyl, —$CO_2H$, $CF_3$, or $OCF_3$. In a preferred aspect the —($C_0$–$C_6$ alkyl)-C(O)$R_{11}$ group is attached to position 4 of the phenyl ring.

In still another aspect, the orientation of bonds 3 and 4 is as follows:

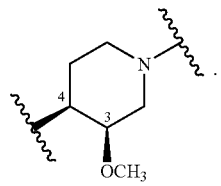

In a preferred aspect, the orientation of bonds 3 and 4 is as follows:

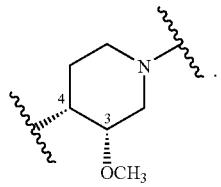

The invention further provides methods for treating emesis, dyspepsia, gastroparesis, constipation, intestinal pseudo-obstruction, gastroesophageal reflux, or post-operative ileus, the method comprising administering a therapeutically effective amount of a compound or salt according of formula (X) to a patient in need of such treatment.

The subject invention provides compounds that are more susceptible to degradation by serum and/or cytosolic esterases than cisapride, thus avoiding the adverse effects associated with metabolism by cytochrome P450.

Advantageously, the therapeutic compounds of the subject invention are stable in storage but have a relatively short half-life in the physiological environment; therefore, the compounds of the subject invention can be used with a lower incidence of side effects and toxicity.

In a preferred aspect of the subject invention, therapeutic stereoisomeric compounds are provided that are useful in the treatment of gastroesophageal reflux disease and that contain an ester group, which is susceptible to degradation by esterases, thereby breaking down the compound and facilitating its efficient removal from the treated individual. In a preferred aspect, the therapeutic stereoisomeric compounds are metabolized by the Phase I drug detoxification system.

A further aspect of the subject invention pertains to the breakdown products (preferably metabolic breakdown products, i.e., metabolites, generally acids of parent esters) that are produced when the therapeutic compounds of the subject invention are acted upon by an esterase. The presence of these breakdown products in the urine or serum can be used to monitor the rate of clearance of the therapeutic compound from a patient.

Degradation of the compounds of the subject invention by esterases is particularly advantageous for drug metabolism because these enzymes are ubiquitously distributed and their activity is not dependent on age, gender, or disease state to the same extent as oxidative hepatic drug metabolism.

The subject invention further provides methods of treating disorders, such as gastroesophageal reflux disease comprising the administration of a therapeutically effective amount of at least one stereoisomeric structural and/or functional analog of cisapride to an individual in need of treatment. In a specific aspect, the subject invention provides stereoisomeric structural and/or functional analogs of cisapride and pharmaceutical compositions of these esterified compounds.

The subject invention further provides materials and methods for the treatment of emesis and such other conditions, including but not limited to dyspepsia, gastroparesis, constipation, and intestinal pseudo-obstruction, while substantially reducing adverse effects associated with the administration of cisapride.

In a preferred aspect of the subject invention, therapeutic stereoisomeric compounds are provided which are useful in the treatment of gastroesophageal reflux, dyspepsia, gastroparesis, constipation, post-operative ileus, and intestinal pseudo-obstruction and which contain an ester group which is acted upon by esterases thereby breaking down the compound and facilitating its efficient removal from the treated individual.

The subject invention further provides methods of synthesizing the unique and advantageous compounds of the subject invention. Particularly, methods of producing and purifying such stereoisomeric compounds are taught. Methods of adding such ester moieties and of producing and purifying stereoisomers, are well known to the skilled artisan and can be readily carried out utilizing the guidance provided herein.

Preferred Compounds

In a preferred aspect, the present invention provides isolated stereoisomers of Compound I, which contains three chiral centers.

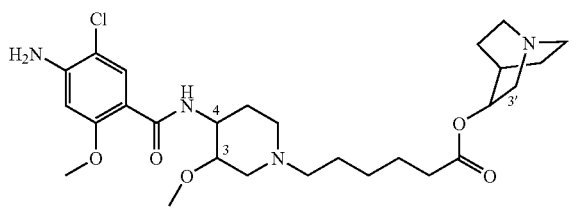

6-[4-(4-Amino-5-chloro-2-methoxy-benzoylamino)-3-methoxy-piperidin-1-yl]-hexanoic acid 1-aza-bicyclo[2.2.2]oct-3-yl ester Compound I Two of the chiral centers exist in cisapride and norcisapride and are in the cis configuration in the active drugs:

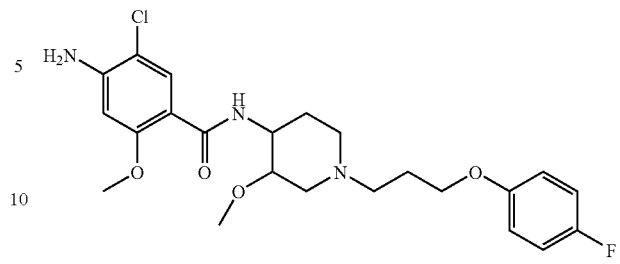

(±)-Cisapride

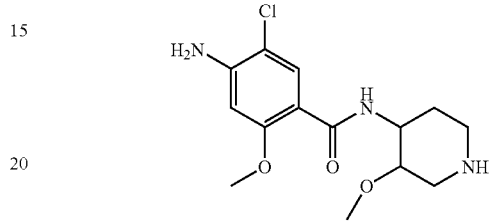

(±)-Norcisapride

Thus, for example, pharmaceutically active norcisapride is a racemic mixture of the two cis enantiomers:

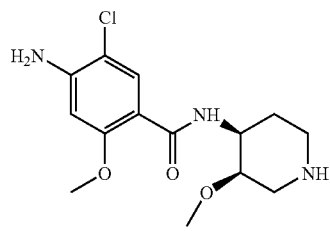

(−)-Norcisapride

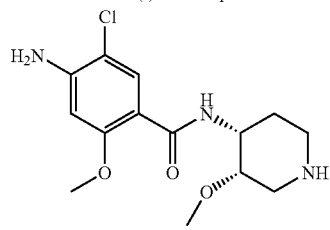

(+)-Norcisapride

In one aspect, the current invention is particularly concerned with the configuration at the third chiral center, in the quinuclidinol moiety. This group is eliminated in the conversion to the acid metabolite referred to herein as ±Compound II Compound II

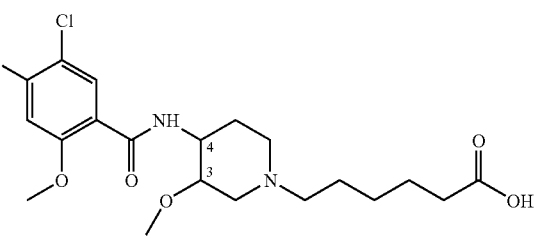

The preferred Compound I stereoisomers of the present invention are made by conjugating R or S quinuclidinol to (+)- or (−)-norcisapride, giving Compounds III, IV, V and VI.

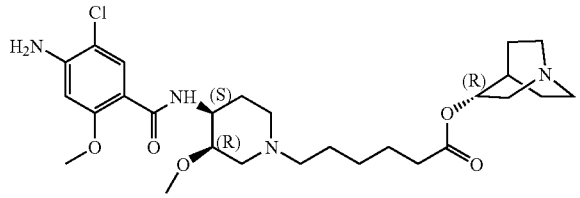

(3R,4S,3'R)-6-[4-(4-Amino-5-chloro-2-methoxy-benzoylamino)-3-methoxy-piperidin-1-yl]-hexanoic acid 1-aza-bicyclo[2.2.2]oct-3-yl ester Compound III: (−)(R)-compound I

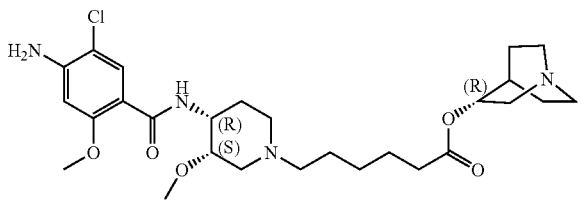

(3S,4R,3'R)-6-[4-(4-Amino-5-chloro-2-methoxy-benzoylamino)-3-methoxy-piperidin-1-yl]-hexanoic acid 1-aza-bicyclo[2.2.2]oct-3-yl ester Compound IV: (+)(R)-compound I

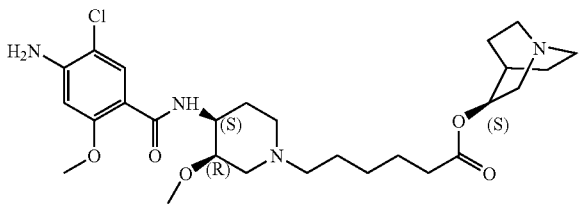

(3R,4S,3'S)-6-[4-(4-Amino-5-chloro-2-methoxy-benzoylamino)-3-methoxy-piperidin-1-yl]-hexanoic acid 1-aza-bicyclo[2.2.2]oct-3-yl Ester Compound V: (−)(S)-compound

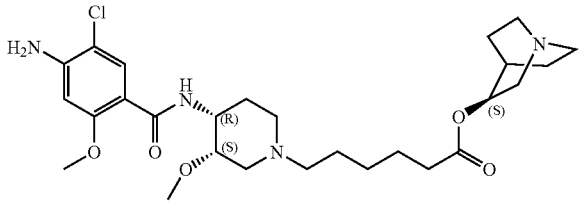

(3S,4R,3'S)-6-[4-(4-Amino-5-chloro-2-methoxy-benzoylamino)-3-methoxy-piperidin-1-yl]-hexanoic acid 1-aza-bicyclo[2.2.2]oct-3-yl Ester Compound VI: (+)(S)-compound I In a preferred aspect, the subject invention pertains to stereoisomerically isolated compounds, and compositions comprising the compounds. The isolated stereoisomeric forms of the compounds of the invention are substantially free from one another (i.e., in stereoisomeric excess). In other words, the "R" forms of the compounds are substantially free from the "S" forms of the compounds and are, thus, in stereoisomeric excess of the "S" forms. Conversely, "S" forms of the compounds are substantially free of "R" forms of the compounds and are, thus, in stereoisomeric excess of the "R" forms. In one aspect of the invention, the isolated stereoisomeric compounds are in at least about 80% stereoisomeric excess. In a preferred aspect, the compounds are in at least about 90% stereoisomeric excess. In a more preferred aspect, the compounds are in at least about 95% stereoisomeric excess. In an even more preferred aspect, the compounds are in at least about 97.5% stereoisomeric excess. In a most preferred aspect, the compounds are in at least about 99% stereoisomeric excess. Similarly, the "(+)" and "(−)" forms of the compounds are also provided in stereoisomeric excess.

As described herein, the various stereoisomers have particular unexpected properties that, advantageously, can be used to customize treatment for a particular set of circumstances. Thus, for example, compounds containing the (3'R)-isomer in the quinuclidinyl ester moiety, i.e., compounds III and IV, are rapidly metabolized by esterases in human plasma, whereas compounds containing the (3'S)-isomer of quinuclidinol, i.e., compounds V and VI, undergo a much slower metabolism.

Thus, the (3'R)-isomers of compound I can be used when a short-duration of action is preferred, for example stimulation of gastric motility in an acute episode, such as pulsatile administration to patients with acute gastroparesis, or in acute gastroesophageal reflux. Another advantage of rapid metabolism by esterases to an substantially less active metabolites, i.e., compound II, is the very low probability of drug-drug interactions and toxicity. Therefore these short-acting (R)-isomers can be advantageously used as an intravenous formulation for treating gastroesophageal reflux in premature newborn who notoriously are not able to metabolize drugs as well as adults because their CYP450 system is not fully developed. In these newborn, a drug having rapid metabolism by a system other than CYP450, e.g., esterases, is a great advantage. On the other hand, the (3'S)-isomers of compound I are best used in chronic situations of the same ailments, for example gastroparesis in diabetic patients or cancer patients under opiates, or in chronic gastroesophageal reflux in patients who need 24-hour coverage.

In addition to their differences in metabolic fate, these separate isomers also have different binding affinities for the 5-HT4 receptor, thus suggesting different activities as well, and therefore different therapeutic uses. Thus, in a decreasing order of affinity for the 5-HT4 receptor, the isomers can be ranked as follows (in parentheses are the binding constant Ki values); compound IV (1.4 nM), compound VI (3.4 nM), compound III (28 nM), and compound V (72 nM). These binding experiments were performed using the radiolabel displacement method described in standard textbooks and easily reproducible by persons skilled in the art of molecular biology.

As a conclusion to these considerations: when the 3 and 4 positions are cis relative to each other, compound I is a mixture of 4 isomers, consisting of 2 pairs of enantiomers. The first pair of enantiomers is (+)(R)-compound I and (−)(S)-compound I (compounds IV and V, respectively), the second pair of enantiomers is (−)(R)-compound I and (+)(S)-compound I (compounds III and VI, respectively). Within each enantiomeric pair, each separate enantiomer has different properties regarding both their rate of hydrolysis by esterases and regarding their affinity at the 5-HT4 receptor. These different properties give them separately advantageous therapeutic uses which are not interchangeable, i.e., which are specific to each isomer, and which are not applicable to the racemic mixture. These differences of affinity at the receptor and these differences in metabolic rates are not predictable and neither is it possible to dissect these properties when testing the racemic mixture.

Definitions

As used herein, the term "alkyl" includes those alkyl groups of a designed number of carbon atoms. Alkyl groups may be straight, or branched. Examples of "alkyl" include methyl, ethyl, propyl, isopropyl, butyl, iso-, sec- and tert-butyl, pentyl, hexyl, heptyl, 3-ethylbutyl, and the like. If the number of carbon atoms is not specified, the subject "alkyl" moiety has from 1 to 6 carbons.

The term "alkoxy" represents an alkyl group of indicated number of carbon atoms attached to the parent molecular moiety through an oxygen bridge. Examples of alkoxy groups include, for example, methoxy, ethoxy, propoxy and isopropoxy.

By "aryl" is meant an aromatic carbocyclic group having a single ring (e.g., phenyl) that is optionally fused or otherwise attached to other aromatic hydrocarbon rings or non-aromatic hydrocarbon rings. "Aryl" includes multiple condensed rings in which at least one is aromatic, (e.g., 1,2,3,4-tetrahydronaphthyl, naphthyl), wherein each ring is optionally mono-, di-, or trisubstituted with the groups identified below, as well as multiple rings that are not fused, such as, for example, biphenyl or binaphthyl. Preferred aryl groups of the present invention are phenyl, 1-naphthyl, 2-naphthyl, indanyl, indenyl, dihydronaphthyl, fluorenyl, tetralinyl or 6,7,8,9-tetrahydro-5H-benzo[a]cycloheptenyl. More preferred are phenyl, biphenyl, and naphthyl. Most preferred is phenyl. The aryl groups herein are unsubstituted or, as specified, substituted in one or more substitutable positions with various groups. For example, such aryl groups may be optionally substituted with, for example, $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono($C_1$–$C_6$)alkylamino($C_1$–$C_6$)alkyl or di($C_1$–$C_6$)alkylamino($C_1$–$C_6$)alkyl.

The term "haloalkoxy" refers to an alkoxy group substituted with at least one halogen atom and optionally further substituted with at least one additional halogen atom, where each halogen is independently F, Cl, Br or I. Preferred halogens are F or Cl. Preferred haloalkoxy groups contain 1–6 carbons, more preferably 1–4 carbons, and still more preferably 1–2 carbons. "Haloalkoxy" includes perhaloalkoxy groups, such as $OCF_3$ or $OCF_2CF_3$.

The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl, and imidazolyl. More preferred heteroaryl groups include pyridyl, pyrrolyl, and indolyl. The heteroaryl groups herein are unsubstituted or, as specified, substituted in one or more substitutable positions with various groups. For example, such heteroaryl groups may be optionally substituted with, for example, $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono($C_1$–$C_6$)alkylamino($C_1$–$C_6$)alkyl or di($C_1$–$C_6$)alkylamino($C_1$–$C_6$)alkyl.

The term "heterocycloalkyl" refers to a ring or ring system containing at least one heteroatom that is preferably selected from nitrogen, oxygen, and sulfur, wherein said heteroatom is in a non-aromatic ring. The heterocycloalkyl ring is optionally fused to or otherwise attached to other heterocycloalkyl rings and/or non-aromatic hydrocarbon rings and/or phenyl rings. Preferred heterocycloalkyl groups have from 3 to 7 members. More preferred heterocycloalkyl groups have 5 or 6 members. Examples of heterocycloalkyl groups include, for example, aza-bicyclo[2.2.2]octyl, aza-bicyclo[3.2.1]octyl, morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide and homothiomorpholinyl S-oxide. Preferred heterocycloalkyl groups include aza-bicyclo[2.2.2]octyl, aza-bicyclo[3.2.1]octyl, piperidinyl, piperazinyl, pyrrolidinyl, thiomorpholinyl, S,S-dioxothiomorpholinyl, morpholinyl, and imidazolidinyl. More preferred are aza-bicyclo[2.2.2]octyl, aza-bicyclo[3.2.1]octyl, piperidinyl, piperazinyl, pyrrolidinyl, imidazolidinyl, and morpholinyl. The heterocycle groups herein are unsubstituted or, as specified, substituted in one or more substitutable positions with various groups. For example, such heterocycle groups may be optionally substituted with, for example, $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$ alkenyl, $C_2$–$C_6$ alkynyl, $C_1$–$C_6$ haloalkyl, $C_1$–$C_6$ haloalkoxy, amino($C_1$–$C_6$)alkyl, mono($C_1$–$C_6$)alkylamino($C_1$–$C_6$)alkyl, di($C_1$–$C_6$)alkylamino($C_1$–$C_6$)alkyl or =O.

The term "pharmaceutically acceptable salts" or "a pharmaceutically acceptable salt thereof" refer to salts prepared from pharmaceutically acceptable non-toxic acids or bases including inorganic acids and bases and organic acids and bases. Since the compound of the present invention is basic, salts may be prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, and the like. Preferred acid addition salts are the chloride and sulfate salts. In the most preferred aspect, structural and/or functional analogs of cisapride are administered as the free base or as the mono or dihydrochloride salt.

As used herein, the terms "treatment" and "treating" encompass prophylactic administration of the compound or a pharmaceutical composition comprising the compound ("prophylaxis") as well as remedial therapy to reduce or eliminate a disease or disorder mentioned herein. Prophylactic administration is intended for prevention of disorders and may be used to treat a subject that is at risk of having or suffering from one or more disorders mentioned herein. Thus, as used herein, the term "treatment", or a derivative thereof, contemplates partial or complete inhibition of the stated disease state, when an active ingredient of the invention is administered prophylactically or following the onset of the disease state for which such active ingredient of the is administered. "Prophylaxis" refers to administration of the active ingredient(s) to a mammal to protect the mammal from any of the disorders set forth herein, as well as others.

The term "therapeutically effective amount" refers to an amount necessary to achieve a derived therapeutic effect such as: 1) an amount sufficient to alleviate reflux disease, 2) an amount sufficient to alleviate nausea and vomiting, or 3) an amount sufficient to alleviate a condition caused by gastrointestinal motility dysfunction. Therapeutically effective amounts of structural and/or functional analogs of cisapride are encompassed by the above-described dosage amounts and dose frequency schedule.

A "mammal" may be, for example, a mouse, rat, pig, horse, rabbit, goat, cow, cat, dog, or human. In a preferred aspect, the mammal is a human.

The term "individual(s)" is defined as a single mammal to which is administered a compound of the present invention. The mammal may be, for example, a mouse, rat, pig, horse, rabbit, goat, cow, cat, dog, or human. In a preferred aspect, the individual is a human.

The term "esterified cisapride" means therapeutic compounds of the subject invention that are structural and/or functional analogs of cisapride, which contain a hydrolysable group, generally an ester, that does not detract from the ability of these compounds to provide a therapeutic benefit, but which makes these compounds more susceptible to degradation by hydrolases, particularly serum and/or cytosolic esterases, and which reduces the interaction of the cytochrome P-450 drug detoxification system with the cisapride compounds. Esterase-mediated metabolism of esterified cisapride compounds reduces the role of the cytochrome P-450 drug detoxification system in cisapride metabolism and reduces or eliminates adverse effects caused by cisapride.

The term "structural analog" as used herein means that a described compound shares structural characteristics with a parent compound. For example, a structural analog of cisapride may share one or more structural characteristics with the parent cisapride compound, such as a substituted aryl ring connected to a piperdine ring through an amide linker, but differ structurally in other ways, such as the inclusion or deletion of one or more other chemical moieties.

The term "functional analog" as used herein means that a described compound shares a functional characteristic with a parent compound. For example, a functional analog of cisapride may share few, if any, structural characteristics with cisapride, but affect a similar function, for example, 5-$HT_4$ agonism.

The term "adverse effects" includes, but is not limited to, gastrointestinal disorders such as diarrhea, abdominal cramping, and abdominal grumbling; tiredness; headache; increased systolic pressure; death; ventricular tachycardia; ventricular fibrillation; torsades de pointes; QT prolongation; increased heart rate; neurological and CNS disorders; and interaction of cisapride with other drugs given concurrently such as but not limited to digoxin, diazepam, ethanol, acenocoumarol, cimetidine, ranitidine, paracetamol, and propranolol.

The term "gastroesophageal reflux disease" as used herein means the incidence of, and the symptoms of, those conditions causing the backward flow of the stomach contents into the esophagus.

The terms "eliciting an anti-emetic effect" and "anti-emetic therapy" as used herein mean providing relief from or preventing the symptoms of nausea and vomiting induced spontaneously or associated with emetogenic cancer chemotherapy or irradiation therapy.

The term "treating a condition caused by gastrointestinal motility dysfunction" as used herein means treating the symptoms and conditions associated with this disorder which include, but are not limited to, gastroesophageal reflux disease, dyspepsia, gastroparesis, constipation, post-operative ileus, and intestinal pseudo-obstruction.

The term "prokinetic" as used herein means the enhancement of peristalsis in, and thus the movement through the gastrointestinal tract.

The term "dyspepsia" as used herein means a condition characterized by an impairment of the power or function of digestion that can arise as a symptom of a primary gastrointestinal dysfunction or as a complication due to other disorders such as appendicitis, gallbladder disturbances, or malnutrition.

The term "gastroparesis" as used herein means a paralysis of the stomach brought about by a motor abnormality in the stomach or as a complication of diseases such as diabetes, progressive systemic sclerosis, anorexia nervosa, or myotonic dystrophy.

The term "constipation" as used herein means a condition characterized by infrequent or difficult evacuation of feces resulting from conditions such as lack of intestinal muscle tone or intestinal spasticity.

The term "post-operative ileus" as used herein means an obstruction in the intestine due to a disruption in muscle tone following surgery.

The term "intestinal pseudo-obstruction" as used herein means a condition characterized by constipation, colicky pain, and vomiting, but without evidence of physical obstruction.

Preparation of Compounds

The chemical synthesis of various analogs of cisapride can be performed by the methods described in European Patent Application No. 0,076,530 A2 published Apr. 13, 1983, U.S. Pat. Nos. 4,962,115 and 5,057,525 and in Van Daele et al., Drug Development Res. 8: 225–232 (1986), the disclosures of which are incorporated herein by reference in their entireties, and modified by the incorporation of an ester group at a point convenient in the synthesis of the disclosed compounds. Exemplary, non-limiting synthesis schemes for certain esterified cisapride analogs of the subject invention are provided in WO 01/093849.

The invention is illustrated further by the following examples, which are not to be construed as limiting the invention in scope or spirit to the specific procedures described in them. Those having skill in the art will recognize that the starting materials may be varied and additional steps employed to produce compounds encompassed by the invention, as demonstrated by the following examples. Those skilled in the art will also recognize that it may be necessary to utilize different solvents or reagents to achieve some of the above transformations. In some cases, protection of reactive functionalities may be necessary to achieve the above transformations. In general, such need for protecting groups, as well as the conditions necessary to attach and remove such groups, will be apparent to those skilled in the art of organic synthesis. When a protecting group is employed, deprotection step may be required. Suitable protecting groups and methodology for protection and deprotection such as those described in *Protecting Groups in Organic Synthesis* by T. Greene are well known and appreciated in the art.

Unless otherwise specified, all reagents and solvents are of standard commercial grade and are used without further purification. The appropriate atmosphere to run the reaction under, for example, air, nitrogen, hydrogen, argon and the like, will be apparent to those skilled in the art.

EXAMPLE 1

Preparation of 6-[4R-(4-amino-5-chloro-2-methoxy-benzoylamino)-3S-methoxy-piperidin-1-yl]-hexanoic acid 1-aza-bicyclo[2.2.2]oct-3'R-yl ester, dihydrochloride salt (ATI-7505 Dihydrochloride Salt)

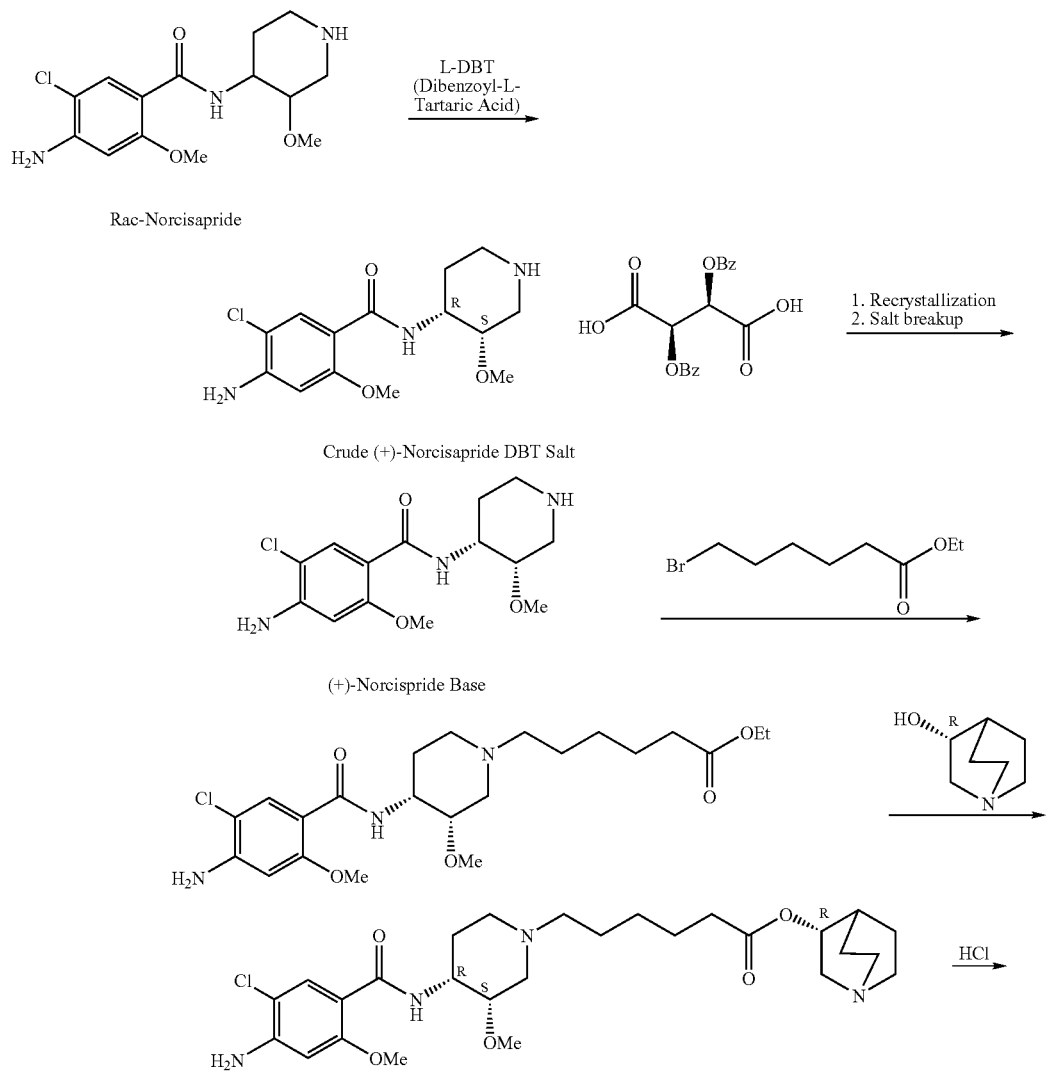

-continued

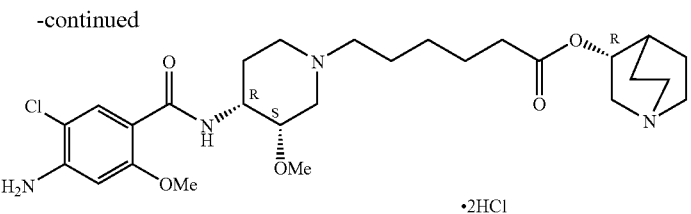

·2HCl

Step 1: Resolution of Racemic Norcisapride (−)-Dibenzoyl-L-tartaric acid ((−)-DBT, about 1 part by weight) was dissolved in ethanol and filtered to remove residual particulates. Separately, racemic norcisapride (about 0.8 part by weight) was dissolved in a mixture of ethanol and water and then filtered. The filtrate was heated to about 75° C. before adding the (−)-DBT solution. After stirring at this temperature for about 30 minutes, the mixture was slowly cooled for several hours to about 5° C. and the product salt was collected under vacuum filtration and washed with EtOH/H$_2$O mixture. The wetcake was recrystallized from EtOH/H$_2$O by heating to about 79° C. and slow cooling to about 5° C. as before. The product was collected on a vacuum filter and washed with EtOH/H$_2$O to give a wetcake.

The wetcake was suspended in water and the pH was adjusted to about 12 using 7% (W/W) aq. NaOH. The resulting suspension was stirred for about 3 hours at room temperature before filtering under vacuum and washing the solid material with water and drying under vacuum. The product was then retreated with (−)-DBT to form the salt by the same general procedure described above. The isolated salt was then neutralized with aq. NaOH as described above. The product was isolated on a filter and dried as before to provide (+)-norcisapride base (about 0.25 parts by weight). The e.e. by chiral HPLC analysis was about 100% (+)-norcisapride. The optical rotation was about +5° (methanol; 25° C. and 589 nm), confirming the positive isomer of norcisapride.

Step 2: Coupling with Ethyl 6-bromohexanoate (+)-Norcisapride (about 1 part by weight), potassium carbonate (about 0.48 part by weight) and potassium iodide (about 0.063 part by weight) were suspended in anhydrous USP ethanol. Ethyl 6-bromohexanoate (about 0.76 part by weight) was added slowly to the suspension at room temperature. The mixture was heated to reflux until completion of the reaction. Subsequent cooling to room temperature the reaction mixture was filtered to remove, e.g., inorganic solids, and the filtrate was concentrated under reduced pressure to about one-half the volume. The product was precipitated by slowly adding the crude material to cold water (about 13 parts by weight) with rapid stirring. The precipitate was filtered under vacuum and washed with water and then reprecipitated twice more by dissolution in anhydrous ethanol and slow addition into cold water as before. The resulting wetcake was washed with n-heptane and resuspended in ethyl acetate and n-heptane (1:9; v/v) and stirred for about 1 hour and before filtering and drying under vacuum to yield 0.73 parts by weight of the coupled product as a white solid.

Step 3: Coupling with (R)-3-Quinuclidinol and Dihydrochloride Salt Formation

The ester (1 part by weight) and (R)-3-Quinuclidinol (about 1.12 part by weight) were suspended in toluene before slowly adding titanium (IV) ethoxide (about 0.5 part by weight) to the stirred suspension. The mixture was heated to about 91° C. under a stream of nitrogen, and partial vacuum was applied to the flask through a distillation apparatus in order to azeotropically remove the ethanol. Additional toluene was added as needed to maintain a minimum solvent volume in the flask. The reaction was considered complete after about 33 hours.

The mixture was cooled to about room temperature and extracted five times with water. The organic layer was concentrated under reduced pressure and the resulting residue was redissolved in EtOH/iPrOH (about 1:1 v/v) and then filtered through a 0.45 micron membrane filter to remove any particulates. Concentrated hydrochloric acid was added slowly to the stirred filtrate to precipitate out the desired product as the dihydrochloride salt. The resulting suspension was stirred for several hours at room temperature and collected under vacuum filtration and rinsed with EtOH/iPrOH (1:1; v/v) to provide 0.53 part by weight of the crude product salt.

Crude dihydrochloride salt was resuspended in ethanol and heated to reflux before cooling to room temperature over about 1 hour. The product was collected under vacuum filtration and rinsed with ethanol and then air-dried. The solids were resuspended in ethanol and warmed to about 55° C. to give a clear solution before adding warm isopropanol and the product was allowed to precipitate by slow cooling to room temperature. The resulting suspension was stirred for several hours before vacuum filtering and rinsing with, e.g., isopropanol. The product was vacuum dried, initially at room temperature for several hours and then at about 55° C. until a constant weight was achieved.

EXAMPLE 2

Preparation of (R)-quinuclidin-3-yl 6-((3S,4R)-4-(4-amino-2-chloro-6-methoxybenzamido)-3-methoxypiperidin-1-yl)hexanoate Step 1: Synthesis of ethyl 4-(dibenzylamino)-3-methoxypiperidine-1-carboxylate (1):

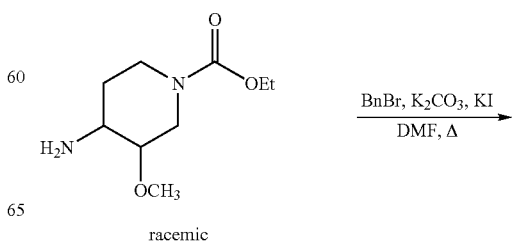

racemic

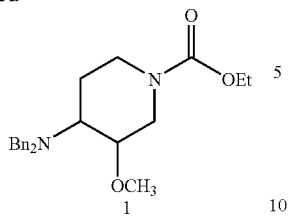

1

To a solution of racemic ethyl 4-amino-3-methoxypiperidine-1-carboxylate (1 part by mole) in DMF were added benzyl bromide (about 2.2 part by mole), potassium carbonate (about 2.4 part by mole) and potassium iodide (about 0.2 part by mole) respectively. The reaction was heated to about 80° C. After about 6 hours, the reaction was slowly diluted with water (about 12 parts by volume) and extracted with, for example, ethyl acetate. The organic layer was washed with brine and then dried over anhyh. Na$_2$SO$_4$. Subsequent filtration and concentration of the solvent provided the 1 as the yellow-orange oil (1 part by mole).

Step 2. Synthesis of N,N-dibenzyl-3-methoxypiperidin-4-amine (2):

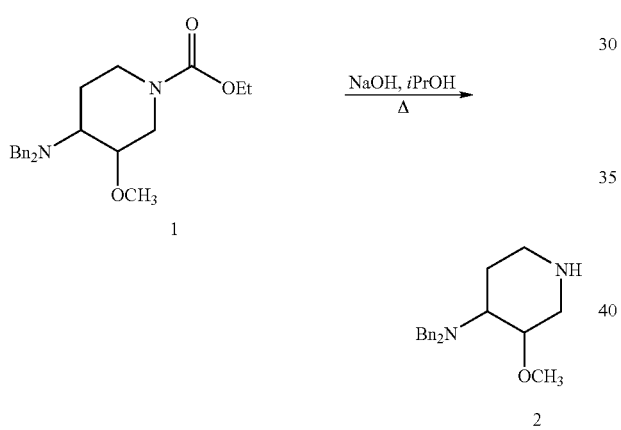

To a solution of 1 was added NaOH (about 10 part by mole) in isopropanol and the mixture was stirred and heated to reflux. After about 3 to about 5 hours, the reaction was cooled to room temperature and the alcoholic solvent was removed via rotary evaporation. The mixture was diluted with water and extracted with ethyl acetate. The organic layer was brined washed before drying over anhyh. Na$_2$SO$_4$. Subsequent filtration and concentration of the solvent provided a crude oil which was purified over SiO$_2$ (CH$_2$Cl$_2$:MeOH:NH$_4$OH; (about) 15:1:0.01) to furnish 2.

Step 3. Synthesis of (3S,4R)-N,N-dibenzyl-3-methoxypiperidin-4-amine (3):

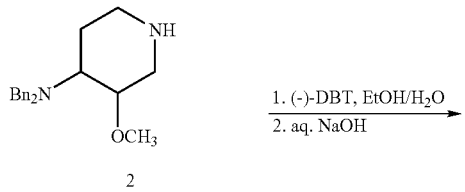

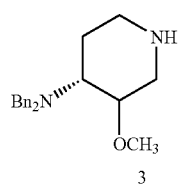

3

(−)-Dibenzoyl-L-tartaric acid (about 1.2 part by weight) is dissolved in ethanol before slowly adding to a solution of 2 (about 1 part by weight). The solution is gently warmed and then allowed to cool to room temperature to crystallize the salt product. The salt is filtered and washed with EtOH/H$_2$O before suspending in water and basifying by adding aq. NaOH (7%, wt/wt) until the pH reaches about 12. The suspension is stirred vigorously at rt and the solid is filtered away, washed with water and vacuum dried to furnish the cis-isomer 3.

Step 4. Synthesis of ethyl 6-((3S,4R)-4-(dibenzylamino)-3-methoxypiperidin-1-yl)hexanoate (4):

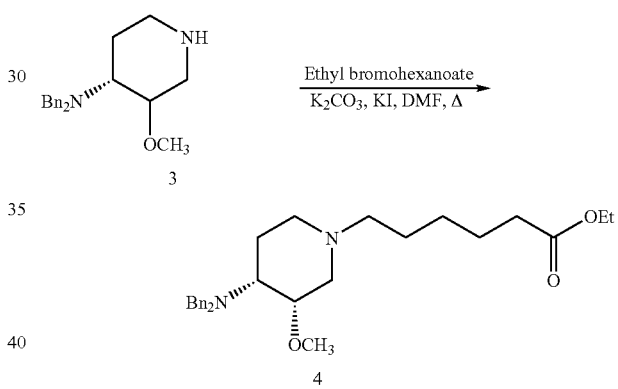

To a solution of 3 (1 part by mole) in DMF are added ethyl bromohexanoate (about 1.2 part by mole), potassium carbonate (about 1.4 part by mole) and potassium iodide (about 0.2 part by mole) respectively. The reaction is then heated to 80° C. After about 8 h, the reaction is slowly diluted with water (about 12 part by volume) and extracted with ethyl acetate. The organic layer is washed with brine and then dried over anhyd. Na$_2$SO$_4$. Subsequent filtration and concentration of the solvent furnishes the crude material. Purification over SiO$_2$ and gives the alkylated material 4.

Step 5. Synthesis of (R)-quinuclidin-3-yl 6-((3S,4R)-4-(dibenzylamino)-3-methoxypiperidin-1-yl)hexanoate (5):

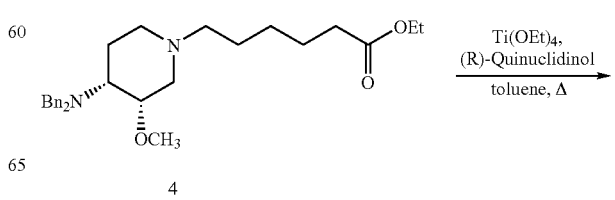

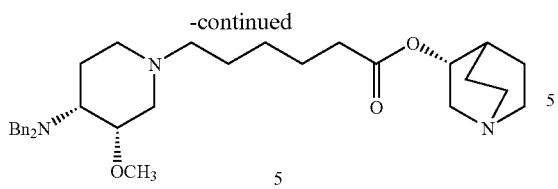

Titanium tetraethoxide is added to a mixture of 4 (1 part by mole) and (R)-(−)-3-quinuclidinol (1 part by mole) in toluene. The reaction mixture is equipped with a dean-stark apparatus before heating to about 90° C. and partial vacuum is then applied (additional toluene is added as needed to main the requisite solvent level). The mixture is then cooled to rt and the reaction is diluted with ethyl acetate and then water is added to the resulting mixture. The organic layer is separated, brine washed, dried over anhyd. Na$_2$SO$_4$, filtered and concentrated. Purification over SiO$_2$ gives the enantiomerically enriched 5.

Step 6. Synthesis of (R)-quinuclidin-3-yl 6-((3S,4R)-4-amino-3-methoxypiperidin-1-yl)hexanoate (6):

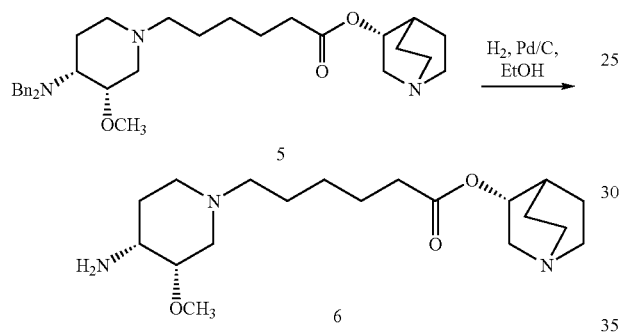

A solution of 5 (1 part by mole) in EtOH is added to a reaction flask containing palladium on carbon (about 0.2 part by mole). The mixture is then evacuated of air before subjecting to hydrogenolysis condition by using atmospheric H$_2$. Upon completion of the reaction, the palladium is filtered off under a pad of celite followed by EtOH washes. The filtrated is concentrated via rotary evaporation to furnish 6.

Step 7. Synthesis of (R)-quinuclidin-3-yl 6-((3S,4R)-4-(4-amino-2-chloro-6-methoxybenzamido)-3-methoxypiperidin-1-yl)hexanoate (7):

To a solution of, for example, ethyl chloroformate (1 part by mole) in THF at about 0° C. is added the benzoic acid (1 part by mole) in portions. The mixture is warmed to rt for about 1 h before cooling to about 0° C. and adding dropwise a solution of 6 (1 part by mole). The reaction is then warmed to rt. Upon completion of the reaction, reaction is quenched by addition of a sat'd solution of NaHCO$_3$ and extracting over EA. The organic layer is brine washed, dried over anhyd. Na$_2$SO$_4$, filtered and concentrated to furnish the desired product 7.

EXAMPLE 3

Alternate Synthesis of ATI-7505

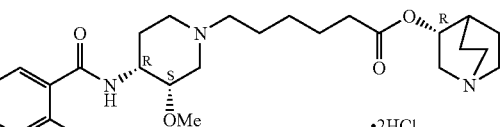

Under acidic conditions, 1-benzylpiperidin-4-one (1) and hydrobromic acid are reacted in the presence of acetic acid to generate N-benzyl-3-bromopiperidin-4-one (2). Treatment of 2 with a sodium methoxide and methanol solution provides 1-benzyl-4,4-dimethoxypiperidin-3-ol (3). [The presence of the beta-amino group negates the possibility of a Favorskii-type reaction.] Methylation of the hydroxyl group is done using a hydride base followed by treatment with iodomethane in the presence of DMF as the solvent to furnish compound 4.

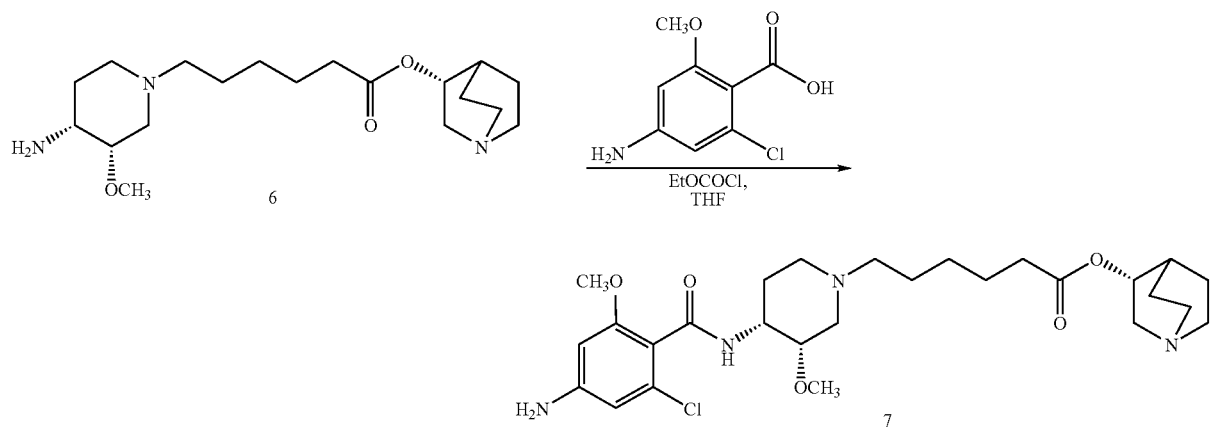

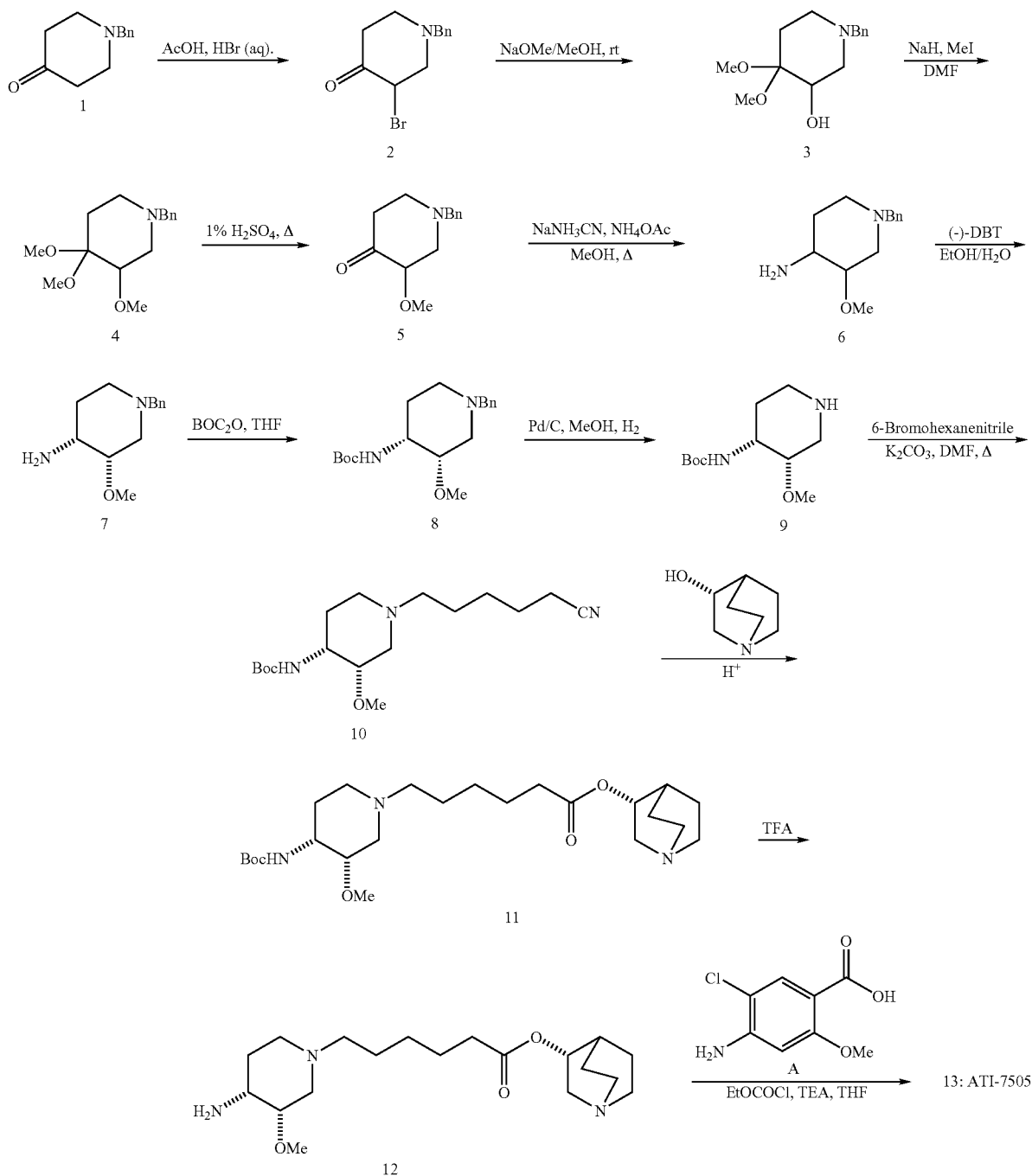

Subsequent acetal hydrolysis using 1% sulfuric acid in the presence of heat yields a piperidine 5, which can then undergo a reductive amination using, for example, sodium cyanoborohydride and ammonium acetate in methanol to yield 1-benzyl-3-methoxypiperidin-4-amine (6). At this stage, 6 can undergo a chiral resolution technique. This can be accomplished, for example, using (−)-DBT or other variant of tartaric acid in the presence of the suitable solvent to afford exclusively asymmetrically pure compound 7. Boc group protection of the primary amine in 7 can be accomplished using Boc anhydride in the presence of THF solvent to obtain 8. A debenzylation reaction by hydrogenolysis using Pd/C in methanol in the presence of atmospheric hydrogen gas set the stage for the alkylation step. Treatment of 6-bromohexanenitrile in the presence of mild base and DMF generates compound 10. A nitrile to ester conversion using (R)-quinuclidinol in the presence of dilute acid generates 11. Subsequent removal of the Boc group using TFA furnishes the free amine, which can undergo a coupling reaction with requisite benzoic acid in the presence of a coupling reagent such as ethyl chloroformate to afford ATI-7505 as an enantiomerically pure material.

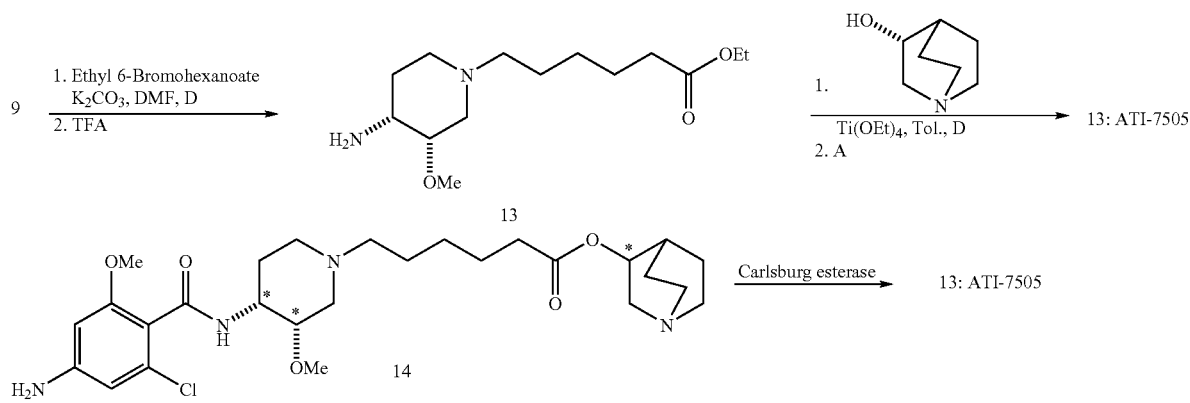

Alternatively, compound 9 can be alkylated using ethyl 6-bromohexanoate in the presence of mild base. Subsequent removal of the Boc group yields compound 13. Titanium mediated transesterification of 13 using (R)-quinuclidinol and titanium tetraethoxide in toluene solvent generates ATI-7505. Carlsburg esterase hydrolyzes esters that are of the S-configuration, therefore leaving intact esters that are of the R configuration. Therefore treatment of diasteriomeric mixtures of 14 with the Carlsburg esterase may also yield ATI-7505.

EXAMPLE 4

(+) and (−)-norcisapride can be made from its racemic mixture by resolution of the enantiomers using conventional means such as optically resolving acids, according to the method described in U.S. Pat. No. 6,147,093, or in "Enantiomers, Racemates and Resolutions", by J. Jacques, A. Collet, and S. H. Wilen (Wiley-Interscience, New York, N.Y.), or in S. H. Wilen et al., Tetrahedron (1977) 33:2725.

The 4 isomers were obtained in low-mg amounts by using preparative column chromatography followed by evaporation of the solvent. This method is useful for preparing small amounts for analytical and characterization purposes. This is a standard separation method used routinely in analytical labs in order to isolate and characterize metabolites.

Possible synthetic routes to Compound IV, Compound VI and (+)-Compound II are described below using (+)-norcisapride as a starting material. The routes to Compound III, Compound V and (−)-Compound II are identical except that they use (−)-norcisapride as a starting material.

EXAMPLE 5

Production of (+)-Compound II, Ethyl Ester

A equimolar mixture of (+)-norcisapride and ethyl 6-bromohexanoate (1 equivalent each), a catalytic amount of KI, and $K_2CO_3$ (2 equivalents) in DMF is heated at about 60 C for several hours or until TLC analysis indicates that the reaction is over. After cooling to room temperature, water is added and the mixture is extracted with EtOAc. The combined organic extracts are washed successively with water, 10% $LiCl_{(aq)}$ solution and brine, then dried over $Na_2SO_4$. Concentration gives (+)-compound II, ethyl ester.

Production of (+)-Compound II

A mixture of crude (+)-compound II, ethyl ester, from above (1 eq.), KOH (2M, 5 eq.) in MeOH and THF (enough to dissolve) is stirred at room temperature for approximately 1 to 2 hours. The MeOH and THF are removed under vacuum, and the residue is diluted with water. Wash with an organic solvent such as EtOAc. The aqueous layer is acidified to pH ~5 using HCl. The precipitate is filtered off and dried to give (+)-Compound II.

Production of Compound IV and Compound VI

A mixture of (+)-Compound II (1 eq.), (R)-(−)-3-quinuclidinol HCl salt (1 eq.), EDAC (1 eq.) and DMAP (1 eq.) in DMF iss heated at around 50 C overnight. After cooling and diluting with water, the mixture is purified by chromatography or by crystallization to provide Compound IV. Similarly, using (S)-(+)-quinuclidinol, Compound VI is obtained.

The following compounds are prepared essentially according to methods and procedures described above. The compound names were generated using either ChemDraw Ultra version 8.03, which is available from Cambridgesoft Corporation or ACD Namepro software, version 6.0.

(3S)-1-azabicyclo[2.2.2]oct-3-yl 6-{(3S,4R)-4-[(4-amino-5-chloro-2-methoxybenzoyl)amino]-3-methoxypiperidin-1-yl}hexanoate;

(3S)-1-azabicyclo[2.2.2]oct-3-yl 6-{(3R,4S)-4-[(4-amino-5-chloro-2-methoxybenzoyl)amino]-3-methoxypiperidin-1-yl}hexanoate;

(3R)-1-azabicyclo[2.2.2]oct-3-yl 6-{(3R,4S)-4-[(4-amino-5-chloro-2-methoxybenzoyl)amino]-3-methoxypiperidin-1-yl}hexanoate;

8-methyl-8-azabicyclo[3.2.1]oct-3-yl 6-{(3S,4R)-4-[(4-amino-5-chloro-2-methoxybenzoyl)amino]-3-methoxypiperidin-1-yl}hexanoate;

4-[({(3S,4R)-4-[(4-amino-5-chloro-2-methoxybenzoyl)amino]-3-methoxypiperidin-1-yl}acetyl)amino]benzoic acid;

methyl 4-[({(3S,4R)-4-[(4-amino-5-chloro-2-methoxybenzoyl)amino]-3-methoxypiperidin-1-yl}acetyl)amino]benzoate;

methyl 4-[({(3S,4R)-4-[(4-amino-5-chloro-2-methoxybenzoyl)amino]-3-methoxypiperidin-1-yl}acetyl)amino]benzoate;

methyl 4-[({(3S,4R)-4-[(4-amino-5-chloro-2-methoxybenzoyl)amino]-3-methoxypiperidin-1-yl}acetyl)amino]benzoate;

ethyl 4-[({(3S,4R)-4-[(4-amino-5-chloro-2-methoxybenzoyl)amino]-3-methoxypiperidin-1-yl}acetyl)amino]benzoate;

isopropyl 4-[({(3S,4R)-4-[(4-amino-5-chloro-2-methoxybenzoyl)amino]-3-methoxypiperidin-1-yl}acetyl)amino]benzoate;
2-methoxyethyl 4-[({(3S,4R)-4-[(4-amino-5-chloro-2-methoxybenzoyl)amino]-3-methoxypiperidin-1-yl}acetyl)amino]benzoate;
2-pyrrolidin-1-ylethyl 4-[({(3S,4R)-4-[(4-amino-5-chloro-2-methoxybenzoyl)amino]-3-methoxypiperidin-1-yl}acetyl)amino]benzoate;
1-methylpiperidin-4-yl 4-[({(3S,4R)-4-[(4-amino-5-chloro-2-methoxybenzoyl)amino]-3-methoxypiperidin-1-yl}acetyl)amino]benzoate;
2-pyridin-2-ylethyl 4-[({(3S,4R)-4-[(4-amino-5-chloro-2-methoxybenzoyl)amino]-3-methoxypiperidin-1-yl}acetyl)amino]benzoate;
2-(dimethylamino)ethyl 4-[({(3S,4R)-4-[(4-amino-5-chloro-2-methoxybenzoyl)amino]-3-methoxypiperidin-1-yl}acetyl)amino]benzoate;
1-methylpiperidin-3-yl 4-[({(3S,4R)-4-[(4-amino-5-chloro-2-methoxybenzoyl)amino]-3-methoxypiperidin-1-yl}acetyl)amino]benzoate;
2-morpholin-4-ylethyl 4-[({(3S,4R)-4-[(4-amino-5-chloro-2-methoxybenzoyl)amino]-3-methoxypiperidin-1-yl}acetyl)amino]benzoate;
1,4-dimethylpiperidin-4-yl 4-[({(3S,4R)-4-[(4-amino-5-chloro-2-methoxybenzoyl)amino]-3-methoxypiperidin-1-yl}acetyl)amino]benzoate;
4-[({(3S,4R)-4-[(4-amino-5-chloro-2-methoxybenzoyl)amino]-3-methoxypiperidin-1-yl}acetyl)amino]benzoic acid;
2-oxo-2-(piperidin-4-ylamino)ethyl 4-[({(3S,4R)-4-[(4-amino-5-chloro-2-methoxybenzoyl)amino]-3-methoxypiperidin-1-yl}acetyl)amino]benzoate;
1-({(3S,4R)-4-[(4-amino-5-chloro-2-methoxybenzoyl)amino]-3-methoxypiperidin-1-yl}acetyl)piperidine-4-carboxylic acid;
methyl 1-({(3S,4R)-4-[(4-amino-5-chloro-2-methoxybenzoyl)amino]-3-methoxypiperidin-1-yl}acetyl)piperidine-4-carboxylate;
methyl 1-({(3S,4R)-4-[(4-amino-5-chloro-2-methoxybenzoyl)amino]-3-methoxypiperidin-1-yl}acetyl)piperidine-4-carboxylate;
methyl 1-({(3S,4R)-4-[(4-amino-5-chloro-2-methoxybenzoyl)amino]-3-methoxypiperidin-1-yl}acetyl)piperidine-4-carboxylate;
ethyl 1-({(3S,4R)-4-[(4-amino-5-chloro-2-methoxybenzoyl)amino]-3-methoxypiperidin-1-yl}acetyl)piperidine-4-carboxylate;
2-methoxyethyl 1-({(3S,4R)-4-[(4-amino-5-chloro-2-methoxybenzoyl)amino]-3-methoxypiperidin-1-yl}acetyl)piperidine-4-carboxylate;
4-{[(2-{(3S,4R)-4-[(4-amino-5-chloro-2-methoxybenzoyl)amino]-3-methoxypiperidin-1-yl}ethyl)(methyl)amino]methyl}benzoic acid;
methyl 4-{[(2-{(3S,4R)-4-[(4-amino-5-chloro-2-methoxybenzoyl)amino]-3-methoxypiperidin-1-yl}ethyl)(methyl)amino]methyl}benzoate;
methyl 4-{[(2-{(3S,4R)-4-[(4-amino-5-chloro-2-methoxybenzoyl)amino]-3-methoxypiperidin-1-yl}ethyl)amino]methyl}benzoate;
isopropyl 4-{[(2-{(3S,4R)-4-[(4-amino-5-chloro-2-methoxybenzoyl)amino]-3-methoxypiperidin-1-yl}ethyl)amino]methyl}benzoate;
ethyl 4-{[(2-{(3S,4R)-4-[(4-amino-5-chloro-2-methoxybenzoyl)amino]-3-methoxypiperidin-1-yl}ethyl)amino]methyl}benzoate Dihydrochloride;
(3R)-1-azabicyclo[2.2.2]oct-3-yl 4-{[(2-{(3S,4R)-4-[(4-amino-5-chloro-2-methoxybenzoyl)amino]-3-methoxypiperidin-1-yl}ethyl)amino]carbonyl}benzoate;
(R)-quinuclidin-3-yl 6-((3S,4R)-4-(4-amino-5-chloro-2-methoxybenzamido)-3-methoxypiperidin-1-yl)hexanoate; or
6-((3S,4R)-4-(4-amino-5-chloro-2-methoxybenzamido)-3-methoxypiperidin-1-yl)hexanoic acid Formulation, Administration and Uses Dosage rates and routes of administration of the disclosed compounds are similar to those already used in the art and known to the skilled artisan (see, for example, Physicians' Desk Reference, 54th Ed., Medical Economics Company, Montvale, N.J., 2000).

The magnitude of a prophylactic or therapeutic dose of structural and/or functional analog of cisapride in the acute or chronic management of diseases and/or disorders described herein will vary with the severity of the condition to be treated, and the route of administration. The dose, and perhaps the dose frequency, will also vary according to the age, body weight, and response of the individual patient. In general, the total daily dose range for structural and/or functional analogs of cisapride, for the conditions described herein, is from about 1 mg to about 200 mg, in single or divided doses. Preferably, a daily dose range should be between about 5 mg to about 100 mg, in single or divided doses, while most preferably, a daily dose range should be between about 5 mg to about 75 mg, in single or divided doses. It is preferred that the doses are administered from 1 to 4 times a day. In managing the patient, the therapy should be initiated at a lower dose, perhaps about 5 mg to about 10 mg, and increased up to about 50 mg or higher depending on the patient's global response. It is further recommended that children, and patients over 65 years, and those with impaired renal or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response.

The compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention are formulated such that an effective amount of the bioactive compound(s) is combined with a suitable carrier in order to facilitate effective administration of the composition.

The compositions of the subject invention include compositions such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets) with the oral solid preparations being preferred over the oral liquid preparations. A preferred oral solid preparation is capsules. The most preferred oral solid preparation is tablets. Preferred amounts of active ingredient (i.e., an structural and/or functional analog of cisapride) in a solid dosage form are about 5 mg, 10 mg, and 25 mg.

Further, acceptable carriers can be either solid or liquid. Solid form preparations include powders, tablets, pills, capsules, cachets, suppositories and dispersible granules. A solid carrier can be one or more substances which may act as diluents, flavoring agents, solubilizers, lubricants, suspending agents, binders, preservatives, tablet disintegrating agents or encapsulating materials.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampules. Also, the unit dosage can be a liquid based preparation or formulated to be incorporated into solid food products, chewing gum, or lozenge.

In addition to the common dosage forms set out above, the compounds of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference in their entirety.

Any suitable route of administration may be employed for providing the patient with an effective dosage of a structural and/or functional analog of cisapride. For example, oral, rectal, parenteral (subcutaneous, intramuscular, intravenous), transdermal, and like forms of administration may be employed. Dosage forms include tablets, troches, dispersions, suspensions, solutions, capsules, patches, and the like.

One aspect of the invention provides a method of treating gastroesophageal reflux disease in a mammal, while substantially reducing the concomitant adverse effects associated with the administration of cisapride, which comprises administering to a human in need of such treatment, a therapeutically effective amount of a structural and/or functional analog of cisapride, or a pharmaceutically acceptable salt thereof. A preferred aspect is the treatment of gastroesophageal reflux disease in humans.

Another aspect of the invention provides a composition for the treatment of a human suffering from gastroesophageal reflux disease, which comprises a therapeutically effective amount of a structural and/or functional analog of cisapride, or a pharmaceutically acceptable salt thereof.

Yet another aspect of the present invention provides a method of eliciting an anti-emetic effect in a mammal, while substantially reducing the adverse effects associated with the administration of cisapride, which comprises administering to a mammal in need of such anti-emetic therapy, a therapeutically effective amount of structural and/or functional analogs of cisapride, or a pharmaceutically acceptable salt thereof. Preferably, the mammal is a human.

In an additional aspect, the present invention encompasses an anti-emetic composition for the treatment of a mammal in need of anti-emetic therapy, which comprises a therapeutically effective amount of a structural and/or functional analog of cisapride, or a pharmaceutically acceptable salt thereof.

A further aspect of the present invention includes a method of treating a condition caused by gastrointestinal motility dysfunction in a mammal which comprises administering to a mammal in need of treatment for gastrointestinal motility dysfunction, a therapeutically effective amount of a structural and/or functional analog of cisapride, or a pharmaceutically acceptable salt thereof. Conditions caused by gastrointestinal motility dysfunction include, but are not limited to, dyspepsia, gastroparesis, constipation, post-operative ileus, and intestinal pseudo-obstruction. Preferably, the mammal is a human.

The observation that cisapride enters the central nervous system and binds to 5HT$_4$ receptors indicates that cisapride may have centrally-mediated effects. Cisapride is a potent ligand at 5HT$_4$ receptors, and these receptors are located in several areas of the central nervous system. Modulation of serotonergic systems has a variety of behavioral effects. Accordingly, the compounds of the subject invention can be used in the treatment of: 1) cognitive disorders, including but not limited to Alzheimer's disease; 2) behavioral disorders, including but not limited to schizophrenia, mania, obsessive-compulsive disorder, and psychoactive substance use disorders; 3) mood disorders, including but not limited to depression and anxiety; and 4) disorders of control of autonomic function, including but not limited to essential hypertension and sleep disorders.

Accordingly, the present invention also provides methods of treating cognitive, behavioral, mood, or autonomic function control disorders in a mammal comprising the administration of a therapeutically effective amount of structural and/or functional analog of cisapride, or a pharmaceutically acceptable salt thereof. Preferably, the mammal is a human.

ATI-7505 Binds with High Affinity to 5-HT$_4$ Receptors

The 5-HT$_4$ receptor is known to be the major receptor subtype involved in the prokinetic activity of cisapride in the gut. ATI-7505 has a high binding affinity for 5-HT$_4$ receptor, with a low nanomolar IC$_{50}$. As shown in Table 1, the affinity of ATI-7505 for the 5-HT$_4$ receptor was 18-fold greater than cisapride and at least 360-fold greater than the ATI-7505 major metabolite, ATI-7500.

TABLE 1

5-HT$_4$ Receptor Binding

| Compound | 5-HT$_4$ Receptor Guinea Pig Striatum | | |
|---|---|---|---|
| | IC$_{50}$ (nM) | K$_I$ (nM) | n$_H$ |
| ATI-7505 | 8.3 | 1.4 | 0.7 |
| ATI-7500 | >3,000 | >500 | — |
| Cisapride | 150 | 24.9 | 0.8 | n$_H$, Hill coefficient.
5-HT$_4$ receptor prototypic reference antagonist [$^3$H]GR113808 (0.70 nM)

ATI-7505 is a Highly Potent Partial Agonist at Human 5-HT$_4$ Receptor

ARYx performed in vitro assays based on adenylyl cyclase stimulation in cells engineered to stably express human 5-HT$_4$ receptor. ATI-7505 proved to be a highly potent 5-HT$_4$ receptor agonist, whereas its major metabolite, ATI-7500 was relatively weak (FIG. 1 and Table 2). The estimated EC$_{50}$ of ATI-7505 (4 nM) was approximately 10-fold lower than that of cisapride (49 nM), and approximately 100-fold lower than that of ATI-7500 (395 nM). Based on its estimated E$_{max}$ value, ATI-7505 had 85% of the efficacy of 5-HT (serotonin) (Table 2), demonstrating that ATI-7505 is a partial agonist of HT$_4$ receptors.

TABLE 2

Potency and Efficacy (Intrinsic Activity) at Human 5-HT$_4$ Receptor

| Compound | Potency | | Efficacy |
|---|---|---|---|
| | EC$_{50}$ | pEC$_{50}$ | % of 5HT (serotonin) |
| 5-HT (serotonin) | 46 | 7 | NA |
| ATI-7505 | 4 | 8.45 | 85 |

TABLE 2-continued

Potency and Efficacy (Intrinsic Activity) at Human 5-HT$_4$ Receptor

| Compound | Potency | | Efficacy |
| --- | --- | --- | --- |
| | EC$_{50}$ | pEC$_{50}$ | % of 5HT (serotonin) |
| ATI-7500 | 395 | 6.40 | 81 |
| Cisapride | 49 | 7 | 77 |

EC$_{50}$, concentration causing 50% maximal increase in adenylyl cyclase activity
pEC$_{50}$, negative logarithm of the EC$_{50}$ A TI-7505 Accelerates Gastric Emptying in Fed Dogs To characterize the effects of ATI-7505 on gastric emptying, experiments were performed in a post-prandial model involving conscious dogs instrumented with sets of strain gauge transducers placed on the stomach and small bowel. The objective of the experiments was to measure the time required for migrating motor contractions (MMCs) to return to baseline following ingestion of a solid meal. A drug-induced shortening of MMC return time indicated an early end of the digestive period due to accelerated gastric emptying. Immediately after completion of an MMC in the mid-small intestine, various doses of test drugs (vehicle, ATI-7505, or cisapride) were infused intravenously (IV) over 20 minutes. At the end of the drug infusion, the dogs were fed a meal. Gut contractions were recorded for a minimum of 60 minutes prior to the start of the drug infusion to establish the fasting state and to identify the onset of MMC in the duodenum, and at least 30 minutes after the return of MMC in the duodenum. Quantitative comparisons of the treatments were based on the time of MMC return as an index of gastric emptying following ingestion of a solid meal. As summarized in FIG. 2, ATI-7505 significantly shortened the time of MMC return, indicating an acceleration of gastric emptying in normal fed dogs. Cisapride showed a similar pattern of action.

ATI-7505 Increases Gastric and Small Intestinal Motor Activity with Negligible Effect on Colonic Activity Experiments were performed in fasted, conscious dogs to evaluate the gastric, small intestinal and colonic motor activity of ATI-7505 compared to cisapride. A specific goal was to determine the dose sizes of ATI-7505 (IV and PO) that most closely mimic the pattern and magnitude of contractile activity caused by cisapride at typical therapeutic doses in dogs (0.5 mg/kg IV; 1 mg/kg PO).

When given IV and PO, both ATI-7505 and cisapride caused prokinetic effects in the dog gut. The onset of action typically occurred within 1 to 2 minutes and 25 to 30 minutes following IV and PO administration, respectively. The effect of ATI-7505 on gastric and small intestinal motor activity mimicked cisapride. Like cisapride, ATI-7505 appeared to cause dose-dependent stimulation of antral and small bowel contractility with relatively little effect on colonic motor activity. The prokinetic effects caused by ATI-7505 in the upper GI tract occurred along with a small but significant (p<0.05) increase in the frequency of giant migrating contractions (GMC).

ATI-7505 was not associated with the development of retrograde giant migrating contractions (RGC). Like cisapride, ATI-7505 had a minimal effect on migrating motor complex (MMC) characteristics in the antrum as well as proximal, mid and distal small intestine. With regard to MMC frequency and phase III duration, only one significant difference was noted: PO ATI-7505 increased MMC frequency in the proximal small intestine relative to the controls. The dogs tolerated the IV and PO doses of ATI-7505 well and exhibited no side effects such as diarrhea, anorexia, or weight loss.

Overall, the results showed that on a mg/kg-basis, ATI-7505 was approximately twice as potent as cisapride. In addition, the actions of ATI-7505, like those of cisapride, were consistent with a mechanism involving the facilitation of acetylcholine release from enteric neurons rather than a direct smooth muscle action. In conclusion, ATI-7505 increases gastric and small intestinal motor activity in a cisapride-like manner with minimal-to-no effect on colonic activity.

The Metabolism of ATI-7505 is CYP450-Independent

Based on data from pooled human microsomes, ATI-7505 undergoes biotransformation to a single metabolite, ATI-7500, which does not appear to be subject to further metabolism. The conversion of ATI-7505 to ATI-7500 was not dependent on the presence of NADPH. Thus the major biotransformation pathway for ATI-7505 occurs independently of CYP450 enzymes.

ATI-7505 Does not Inhibit CYP450 Enzymes

To test the potential for ATI-7505 and/or its main metabolite, ATI-7500 to act as CYP450 inhibitors, these two molecules were screened using Gentest Supersomes™. Consistent with published reports, cisapride had significant inhibitory activity against CYP450 enzyme isoforms, CYP3A4, 2D6 and to a lesser extent 2C$_9$. Neither ATI-7505 nor its primary metabolite, ATI-7500 displayed significant inhibitory activity against these three CYP450 isoforms, nor against a panel of other isoforms known to play a role in drug metabolism.

ATI-7505 Has Negligible Affinity for the Cardiac Channel, I$_{Kr}$

The rapidly activating delayed rectifier potassium (K+) current in humans (human I$_{Kr}$) is a K+ channel that is encoded by the human-ether-a-go-go-related gene (hERG). Cisapride is known to produce QT interval prolongations via a blockade of I$_{Kr}$, and it was therefore of interest to determine if ATI-7505 and ATI-7500 have important inhibitory effects on human I$_{Kr}$. The test system was mammalian HEK-293 cells expressing the HERG K+ channels, in which the potassium current was measured by whole cell patch-clamp technique. The ranking of the IC$_{50}$ values was: cisapride (9.5 nM)>ATI-7505 (24,521 nM)>ATI-7500 (204,080 nM) (Table 3). Overall, the findings indicate that ATI-7505 has a significantly lower pro-arrhythmic potential than cisapride and suggest that both ATI-7505 and ATI-7500 have negligible affinity for human I$_{Kr}$ channels.

TABLE 3

Inhibition of I$_{Kr}$ Activity

| | Activity of I$_{Kr}$ in HEK Cells | |
| --- | --- | --- |
| Compound | % I$_{Kr}$ control (10,000 nM) | IC$_{50}$ |
| ATI-7505 | 78.0 | 24521 |
| ATI-7500 | 88.9 | 204080 |
| Cisapride | 0 | 9.5 |

Data are normalized to % control tail I$_{Kr}$ (current elicited without drug or vehicle present)

ATI-7505 Does not Induce Important Electrophysiological Changes in Guinea Pig Hearts The cardiac electrophysiological effects of ATI-7505 were examined in isolated, perfused guinea pig hearts. The study examined ATI-7505, ATI-7500 and cisapride, all of which were each tested at concentrations up to 10,000 nM. The no observed effect level (NOEL) was defined as the highest concentration of test compound not showing a response that was significantly different from baseline (p<0.05). The following 6 cardiac parameters were tested: (1) QT interval; (2) MAPD$_{90}$; (3) SA interval; (4) QRS interval; (5) AH interval; and (6) HV. While ATI-7505 was a very weak modulator of cardiac electrophysiologic parameters, its metabolite, ATI-7500 entirely lacked electrophysiological activity (Table 4). The NOEL for ATI-7500 was >10,000 nM for the entire set of 6 cardiovascular parameters. Since cisapride had a NOEL of 10 nM for the combined set of 6 cardiac parameters tested, while ATI-7505 had a combined NOEL of 1,000 nM, ATI-7505 appears to lack the potency of cisapride in modulating cardiac electrophysiologic parameters. Overall, the findings demonstrate that ATI-7505 is significantly safer than cisapride with regard to the potential to induce important cardiac electrophysiologic fluctuations.

TABLE 4

Cardiac Electrophysiologic Parameters in Isolated Perfused

| Electrophysiological Parameter | No Observed Effect Level (NOEL) | | |
|---|---|---|---|
| | Cisapride | ATI-7505 | ATI-7500 |
| QT Interval | 10 | 1,000 | >10,000 |
| MAPD$_{90}$ | 10 | 1,000 | >10,000 |
| SA Interval | 100 | >10,000 | >10,000 |
| QRS Interval | 1,000 | >10,000 | >10,000 |
| AH Interval | 1,000 | >10,000 | >10,000 |
| HV Interval | 1,000 | 1,000 | >10,000 |
| Combined Parameters | 10 | 1,000 | >10,000 |

All molecules were tested at baseline, 10, 100, 1,000, and 10,000 nM. Other than for values reported as >10,000 nM, a significant difference (p < 0.05) from baseline was observed when the molecule was tested at a 10-fold higher Metabolism in Human Microsomal Preparations The metabolism of these compounds was studied in pooled human microsomes in the presence and absence of the Cytochrome P-450 cofactor NADPH and both the disappearance of parent and the appearance of the corresponding acid metabolite, i.e., the corresponding compound-II isomer, monitored with time.

As shown in Table 5, Compounds III and IV were rapidly hydrolyzed by esterase to their respective metabolites (+) and (−)-Compound II. The metabolism was not dependent on CYP450 since the rate of hydrolysis was independent on NADPH presence, which is a necessary cofactor for CYP450 to function. In contrast, (±)-S Compounds V and VI appeared to be quite stable with time under the same conditions. In this experiment, the amount of substrate (compounds III, IV, V, and VI) remaining in the reaction after 5, 60, and 90 minutes were evaluated by a tandem HPLC-MS method. This remaining amount was correlated with the appearance of the metabolite compound II. The sum of remaining substrate and compound II was constant over time and equal to the amount of starting material at time zero, therefore indicating that hydrolysis was the only metabolic reaction taking place.

TABLE 5 test compounds were incubated in pooled human microsomal preparation in the presence of NADPH cofactor. The remaining amount of test compound and the appearance of the metabolite compound II were monitored over 90 minutes.

| | Test compound | | | | | |
|---|---|---|---|---|---|---|
| | Compounds III and IV | | | Compound V and VI | | |
| Time | Remaining Test Compound (ng/mL) | Metabolite (ng/mL) | Sum | Remaining Test Compound (ng/mL) | Metabolite (ng/mL) | Sum |
| 5 | 31.3 | 2 | 33.3 | 32.9 | 1.5 | 34.4 |
| 60 | 20.7 | 14.5 | 35.2 | 29.9 | 1.5 | 31.4 |
| 90 | 16.9 | 19.4 | 36.3 | 31.9 | 1.5 | 33.4 |

Metabolism in Fresh Human Blood.

Test compounds were dissolved in DMSO to make 12.5 mM stock solution and diluted with water to a final concentration of 2.5 mM (DMSO/H2O=20/80). Fresh blood was collected into heparinized tubes from 3 human donors and blood was stored on ice until incubation. Separate aliquots of blood from each donor were pipetted into 1.5 mL centrifuge tubes and the tubes were pre-incubated in a shaking water bath at 37° C. for 5 minutes. The reaction was initiated by the addition of 10 μL of the appropriate test compound stock to each tube (final concentration=100 μM). Incubations were quenched after 0, 5, 15, 30 and 60 minutes, by the addition of acetonitrile (750 mL), centrifuged at 12,000 rpm for 2 minutes and the supernatant analyzed on an Agilent 1100 HPLC system. Separations were accomplished on a Keystone Intersil ODS2, 250×4.6 mm, 5 m column. The aqueous mobile phase consisted of 20 mM ammonium acetate buffer (pH 5.7) and the organic phase acetonitrile. A gradient was used: initial condition consisted of 20% acetonitrile for 1 minute. The acetonitrile concentration was increased linearly to 90% over the next 8 minutes and held there for 1 minute. The system was then recycled to initial conditions over the course of 1 minute and held there for 4 minutes before the next injection. The peak area for the parent peak was determined by monitoring absorbance at 240, 254 and 290 nM. The results were expressed as amount of initial compound remaining and data subjected to kinetic analysis using WinNonLin. The half-lives for the individual compounds are given below in Table 6.

TABLE 6

| | Diastereomeric Configuration | | |
|---|---|---|---|
| Compound | Norcis "half" | Quinuclindol "half" | Half-life (min) |
| III | – | R | |
| Subject 1 | | | 12.03 |
| Subject 2 | | | 10.37 |
| Subject 3 | | | 9.23 |

TABLE 6-continued

| Compound | Diastereomeric Configuration | | Half-life (min) |
| --- | --- | --- | --- |
| | Norcis "half" | Quinuclindol "half" | |
| Mean ± SD | | | 10.5 ± 1.41 |
| IV | + | R | |
| Subject 1 | | | 8.47 |
| Subject 2 | | | 8.61 |
| Subject 3 | | | 8.58 |
| Mean ± SD | | | 8.59 ± 0.077 |
| V | − | S | |
| Subject 1 | | | >60 min |
| Subject 2 | | | >60 min |
| Subject 3 | | | >60 min |
| VI | + | S | |
| Subject 1 | | | >60 min |
| Subject 2 | | | >60 min |
| Subject 3 | | | >60 min |

It should be understood that the examples and aspects described herein are for illustrative purposes only and that various modifications or changes in light thereof will be suggested to persons skilled in the art and are to be included within the spirit and purview of this application and the scope of the appended claims. Further, all patents, patent applications, provisional applications, and publications referred to or cited herein are incorporated by reference in their entirety to the extent they are not inconsistent with the explicit teachings of this specification.

The invention and the manner and process of making and using it, are now described in such full, clear, concise and exact terms as to enable any person skilled in the art to which it pertains, to make and use the same. It is to be understood that the foregoing describes preferred aspects of the invention and that modifications may be made therein without departing from the spirit or scope of the invention as set forth in the claims. To particularly point out and distinctly claim the subject matter regarded as invention, the following claims conclude this specification.

What is claimed is:

1. A compound selected from

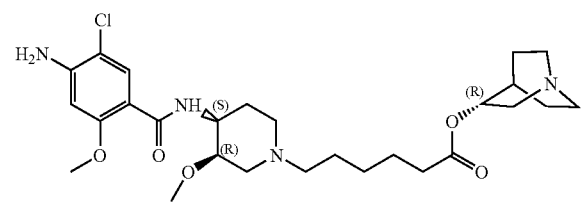

(3R,4S,3'R)-6-[4-(4-Amino-5-chloro-2-methoxy-benzoylamino)-3-methoxy-piperidin-1-yl]-hexanoic acid 1-aza-bicyclo[2.2.2]oct-3-yl ester
and pharmaceutically acceptable salts thereof.

2. A compound selected from

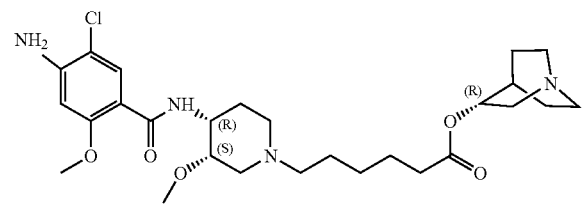

(3S,4R,3'R)-6-[4-(4-Amino-5-chloro-2-methoxy-benzoylamino)-3-methoxy-piperidin-1-yl]-hexanoic acid 1-aza-bicyclo[2.2.2]oct-3-yl ester
and pharmaceutically acceptable salts thereof.

3. A compound selected from

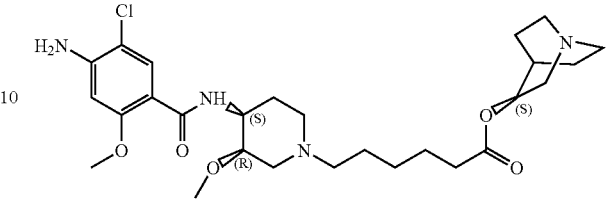

(3R,4S,3'S)-6-[4-(4-Amino-5-chloro-2-methoxy-benzoylamino)-3-methoxy-piperidin-1-yl]-hexanoic acid 1-aza-bicyclo[2.2.2]oct-3-yl ester
and pharmaceutically acceptable salts thereof.

4. A compound selected from

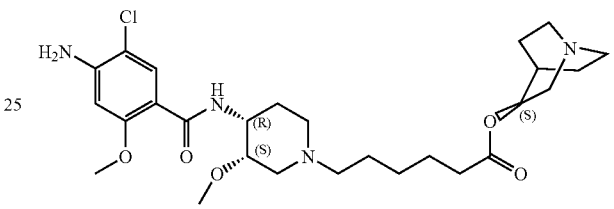

(3S,4R,3'S)-6-[4-(4-Amino-5-chloro-2-methoxy-benzoylamino)-3-methoxy-piperidin-1-yl]-hexanoic acid 1-aza-bicyclo[2.2.2]oct-3-yl ester
and pharmaceutically acceptable salts thereof.

5. The composition according to claim 1 wherein the compound is a dihydrochloride salt form.

6. The composition according to claim 2 wherein the compound is a dihydrochloride salt form.

7. The composition according to claim 3 wherein the compound is a dihydrochloride salt form.

8. The composition according to claim 4 wherein the compound is a dihydrochloride salt form.

9. A composition comprising the compound according to claim 1 wherein the compound is present in at least about 90% stereoisomeric excess.

10. A composition comprising the compound according to claim 2 wherein the compound is present in at least about 90% stereoisomeric excess.

11. A composition comprising the compound according to claim 3 wherein the compound is present in at least about 90% stereoisomeric excess.

12. A composition comprising the compound according to claim 4 wherein the compound is present in at least about 90% stereoisomeric excess.

13. A composition comprising the compound according to claim 5 wherein the compound is present in at least about 90% stereoisomeric excess.

14. A composition comprising the compound according to claim 6 wherein the compound is present in at least about 90% stereoisomeric excess.

15. A composition comprising the compound according to claim 7 wherein the compound is present in at least about 90% stereoisomeric excess.

16. A composition comprising the compound according to claim 8 wherein the compound is present in at least about 90% stereoisomeric excess.

17. A composition comprising the compound according to claim 1 and a pharmaceutically acceptable excipient, adjuvant, carrier, or solvent.

18. A composition comprising the compound according to claim 2 and a pharmaceutically acceptable excipient, adjuvant, carrier, or solvent.

19. A composition comprising the compound according to claim 3 and a pharmaceutically acceptable excipient, adjuvant, carrier, or solvent.

20. A composition comprising the compound according to claim 4 and a pharmaceutically acceptable excipient, adjuvant, carrier, or solvent.

21. A composition comprising the composition according to claim 5 and a pharmaceutically acceptable excipient, adjuvant, carrier, or solvent.

22. A composition comprising the composition according to claim 6 and a pharmaceutically acceptable excipient, adjuvant, carrier, or solvent.

23. A composition comprising the composition according to claim 7 and a pharmaceutically acceptable excipient, adjuvant, carrier, or solvent.

24. A composition comprising the composition according to claim 8 and a pharmaceutically acceptable excipient, adjuvant, carrier, or solvent.

25. A composition comprising the compound according to claim 9 and a pharmaceutically acceptable excipient, adjuvant, carrier, or solvent.

26. A composition comprising the compound according to claim 10 and a pharmaceutically acceptable excipient, adjuvant, carrier, or solvent.

27. A composition comprising the compound according to claim 11 and a pharmaceutically acceptable excipient, adjuvant, carrier, or solvent.

28. A composition comprising the compound according to claim 12 and a pharmaceutically acceptable excipient, adjuvant, carrier, or solvent.

29. A composition comprising the composition according to claim 13 and a pharmaceutically acceptable excipient, adjuvant, carrier, or solvent.

30. A composition comprising the composition according to claim 14 and a pharmaceutically acceptable excipient, adjuvant, carrier, or solvent.

31. A composition comprising the composition according to claim 15 and a pharmaceutically acceptable excipient, adjuvant, carrier, or solvent.

32. A composition comprising the composition according to claim 16 and a pharmaceutically acceptable excipient, adjuvant, carrier, or solvent.

* * * * *

UNITED STATES PATENT AND TRADEMARK OFFICE
CERTIFICATE OF CORRECTION

PATENT NO.        : 7,176,218 B2  
APPLICATION NO. : 11/031623  
DATED             : February 13, 2007  
INVENTOR(S)      : Ian Irwin, Monica Palme and Cyrus Becker It is certified that error appears in the above-identified patent and that said Letters Patent is hereby corrected as shown below:

On the Title Page, Item (75) replace "Monica Palme, San Jose, CA (US);" with -- Monica Palme, San Jose, CA (Canada); --.

Signed and Sealed this

Eighth Day of July, 2008

JON W. DUDAS  
*Director of the United States Patent and Trademark Office*

UNITED STATES PATENT AND TRADEMARK OFFICE
CERTIFICATE OF CORRECTION

PATENT NO. : 7,176,218 B2  Page 1 of 1
APPLICATION NO. : 11/031623
DATED : February 13, 2007
INVENTOR(S) : Irwin et al.

It is certified that error appears in the above-identified patent and that said Letters Patent is hereby corrected as shown below:

In Column 44, line 35, claim 5: delete "composition" and insert --compound--
In Column 44, line 37, claim 6: delete "composition" and insert --compound--
In Column 44, line 39, claim 7: delete "composition" and insert --compound--
In Column 44, line 41, claim 8: delete "composition" and insert --compound--
In Column 45, line 13, claim 21: delete the second occurrence of the term "composition" and replace it with --compound--
In Column 45, line 16, claim 22: delete the second occurrence of the term "composition" and replace it with --compound--
In Column 45, line 19, claim 23: delete the second occurrence of the term "composition" and replace it with --compound--
In Column 45, line 22, claim 24: delete the second occurrence of the term "composition" and replace it with --compound--
In Column 45, line 25, claim 25: delete "compound" and replace it with --composition--
In Column 46, line 1, claim 26: delete "compound" and replace it with --composition--
In Column 46, line 4, claim 27: delete "compound" and replace it with --composition--
In Column 46, line 7, claim 28: delete "compound" and replace it with --composition--

Signed and Sealed this

Seventh Day of December, 2010

David J. Kappos
*Director of the United States Patent and Trademark Office*

UNITED STATES PATENT AND TRADEMARK OFFICE
Certificate

Patent No. 7,176,218 B2                                                            Patented: February 13, 2007

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Ian Irwin, Palo Alto, CA (US); Monica Palme, San Jose, CA (US); Cyrus Becker, San Francisco, CA (US); and Pascal J. Druzgala, Santa Rosa, CA (US).

Signed and Sealed this Seventh Day of January 2014.

JANET L. ANDRES
Supervisory Patent Examiner
Art Unit 1625
Technology Center 1600